(12) United States Patent
Gazeley et al.

(10) Patent No.: US 12,076,537 B2
(45) Date of Patent: Sep. 3, 2024

(54) INJECTION DEVICE AND DETECTOR ARRANGEMENT

(71) Applicant: Sanofi, Paris (FR)

(72) Inventors: Oliver Charles Gazeley, Warwick (GB); Gavin Newman, Warwick (GB); Aidan Michael O'Hare, Warwick (GB); David Aubrey Plumptre, Warwick (GB); Robert Veasey, Warwick (GB); Craig Ashley Mason, Warwick (GB); Anthony Paul Morris, Warwick (GB)

(73) Assignee: Sanofi, Paris (FR)

( * ) Notice: Subject to any disclaimer, the term of this patent is extended or adjusted under 35 U.S.C. 154(b) by 687 days.

(21) Appl. No.: 17/299,931

(22) PCT Filed: Dec. 16, 2019

(86) PCT No.: PCT/EP2019/085294
§ 371 (c)(1),
(2) Date: Jun. 4, 2021

(87) PCT Pub. No.: WO2020/127006
PCT Pub. Date: Jun. 25, 2020

(65) Prior Publication Data
US 2022/0152312 A1    May 19, 2022

(30) Foreign Application Priority Data

Dec. 18, 2018  (EP) .................................... 18306710

(51) Int. Cl.
*A61M 5/315*         (2006.01)
(52) U.S. Cl.
CPC .... *A61M 5/31535* (2013.01); *A61M 5/31526* (2013.01); *A61M 5/31528* (2013.01);
(Continued)

(58) Field of Classification Search
None
See application file for complete search history.

(56) References Cited

U.S. PATENT DOCUMENTS

2008/0319383 A1    12/2008  Byland et al.
2016/0220754 A1    8/2016   Shaanan et al.

FOREIGN PATENT DOCUMENTS

CN        102202711        9/2011
CN        104902945        9/2015
(Continued)

OTHER PUBLICATIONS

PCT International Search Report and Written Opinion in International Application No. PCT/EP2019/085294 , dated Feb. 20, 2020, 13 pages.
(Continued)

*Primary Examiner* — Manuel A Mendez
(74) *Attorney, Agent, or Firm* — Bond, Schoeneck & King, PLLC

(57) ABSTRACT

The disclosure relates to an injection device for setting and injecting pre-set or user-selectable doses of a medicament, the injection device comprising an elongated housing defining a longitudinal direction and configured to accommodate a cartridge containing the medicament, and a detector arrangement operable to detect a relative movement between a first element and a second element. The first element is subject to a first movement relative to the second element along a first longitudinal direction for setting of a dose, the first element is subject to a second movement relative to the second element along a second longitudinal direction for dispensing of the dose, one of the first movement and the second movement is a helical movement, and the other one of the first movement and the second movement is a sliding movement in the longitudinal direction. The second element (Continued)

comprises at least one reference element fixed to the second element.

20 Claims, 17 Drawing Sheets

(52) U.S. Cl.
CPC .... *A61M 5/31546* (2013.01); *A61M 5/31568* (2013.01); *A61M 2205/3327* (2013.01); *A61M 2205/6027* (2013.01)

(56) References Cited

FOREIGN PATENT DOCUMENTS

| | | |
|---|---|---|
| CN | 104936641 | 9/2015 |
| CN | 105764550 | 7/2016 |
| CN | 107405449 | 11/2017 |
| CN | 107405453 | 11/2017 |
| JP | 2006-519074 A | 8/2006 |
| JP | 2012-507314 A | 3/2012 |
| JP | 2016-502900 A | 2/2016 |
| WO | WO 2004/078239 | 9/2004 |
| WO | WO 2004/078240 | 9/2004 |
| WO | WO 2004/078241 | 9/2004 |
| WO | WO 2010/052275 | 5/2010 |
| WO | WO 2013/010893 | 1/2013 |
| WO | WO 2013/034716 | 3/2013 |
| WO | WO 2013/111343 | 7/2014 |
| WO | WO 2014/111335 | 7/2014 |
| WO | WO 2014/111343 | 7/2014 |
| WO | WO 2015/075136 | 5/2015 |
| WO | WO 2016/142216 | 9/2016 |
| WO | WO 2016/142511 | 9/2016 |
| WO | WO 2017/186841 | 11/2017 |
| WO | WO 2020127006 | 6/2020 |

OTHER PUBLICATIONS

International Preliminary Report on Patentability in International Appln. No. PCT/EP2019/085294, dated Jul. 1, 2021, 10 pages.

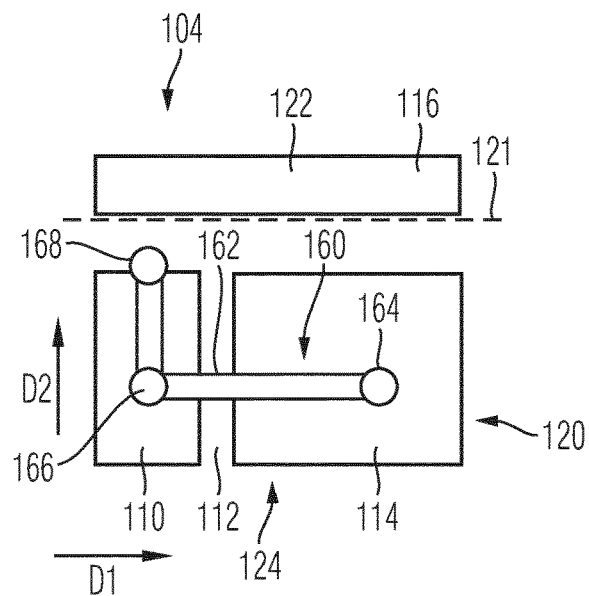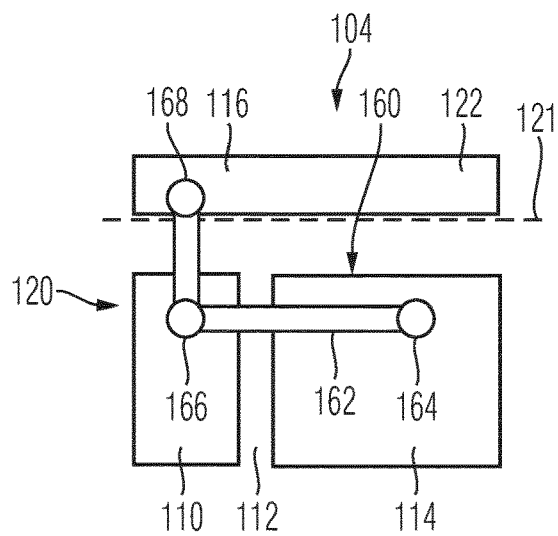
Fig. 22
Fig. 23
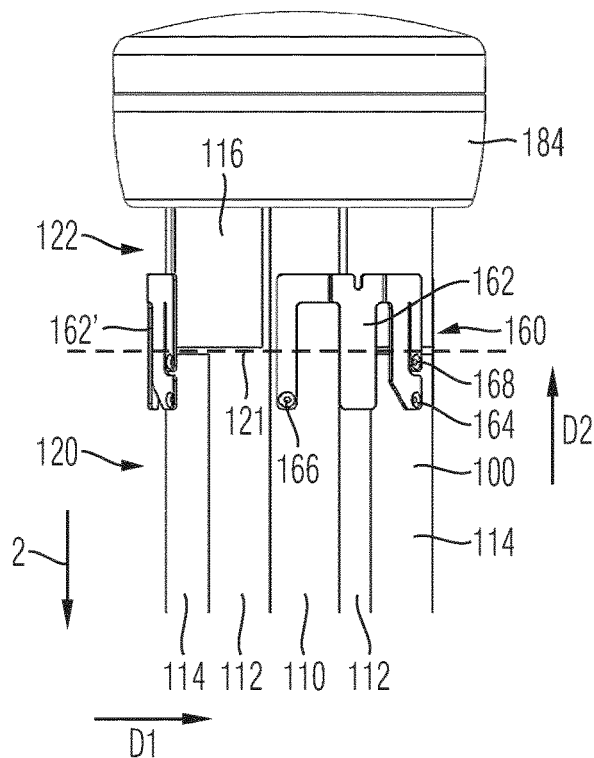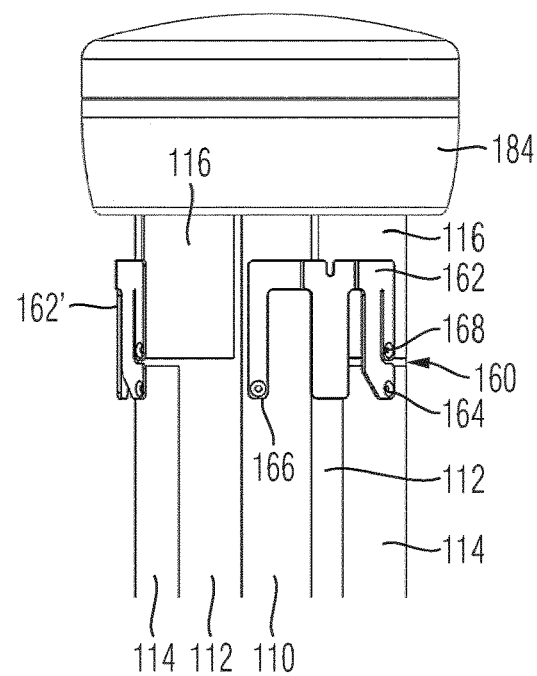
Fig. 24
Fig. 25

INJECTION DEVICE AND DETECTOR ARRANGEMENT

CROSS REFERENCE TO RELATED APPLICATIONS

The present application is the national stage entry of International Patent Application No. PCT/EP2019/085294, filed on Dec. 16, 2019, and claims priority to Application No. EP 18306710.7, filed on Dec. 18, 2018, the disclosures of which are incorporated herein by reference.

TECHNICAL FIELD

The present disclosure relates in one aspect to an injection device, such as a pen-type injector for expelling of preset or user-selectable doses of a medicament. In particular, the disclosure relates to an injection device comprising a detector arrangement operable to detect or to quantitatively measure a size of a dose actually set or dispensed by the injection device.

BACKGROUND

Injection devices for setting and dispensing a single or multiple doses of a liquid medicament are as such well-known in the art. Generally, such devices have substantially a similar purpose as that of an ordinary syringe.

Injection devices, in particular pen-type injectors have to meet a number of user-specific requirements. For instance, with patient's suffering chronic diseases, such as diabetes, the patient may be physically infirm and may also have impaired vision. Suitable injection devices especially intended for home medication therefore need to be robust in construction and should be easy to use. Furthermore, manipulation and general handling of the device and its components should be intelligible and easily understandable. Moreover, a dose setting as well as a dose dispensing procedure should be easy to operate and unambiguous.

Typically, such devices comprise a housing including a particular cartridge holder, adapted to receive a cartridge at least partially filled with the medicament to be dispensed. Such devices further comprise a drive mechanism or expelling mechanism, usually having a displaceable piston rod which is configured to operably engage with a piston of the cartridge. The drive mechanism and the piston rod are operable to displace the piston of the cartridge in a distal direction or dispensing direction and may therefore expel a predefined amount of the medicament via a piercing assembly, which is to be releasably coupled with a distal end section of the housing of the injection device.

The medicament to be dispensed by the injection device is typically provided and contained in a multi-dose cartridge. Such cartridges typically comprise a vitreous barrel sealed in a distal direction by means of a pierceable seal and being further sealed in proximal direction by the piston. With reusable injection devices an empty cartridge is replaceable by a new one. In contrast to that, injection devices of disposable type are to be discarded when the medicament in the cartridge has been dispensed or used-up.

Some injection devices are mechanically and/or manually implemented. Here, a user has to set a dose by manually operating a dose dial, e.g. by way of rotating or sliding the dose dial relative to a housing of the injection device. For dispensing or expelling of the dose the user has to displace the dial and/or a trigger in an opposite direction. There exist pen-type injection devices, e.g. disclosed in WO 2004/078239 A1, WO 2004/078240 A1 or WO 2004/078241 A1 having a dial extension, which is subject to a combined rotational and longitudinal displacement in proximal direction for setting of a dose and further being subject to a sliding displacement into an opposite longitudinal direction, i.e. distal direction for dispensing or expelling of the dose of the medicament. With manually operated injection devices a user has to exert a driving force onto a trigger, e.g. implemented as a dose button or trigger button. The drive mechanism is typically operable to transfer a driving force exerted by the user into a distally directed driving motion of the piston rod that is operably engaged with the piston or stopper of the cartridge filled with a medicament.

The dial extension, e.g. an assembly of numerous components of an injection device that is displaceable relative to a housing at least for the purpose of dose setting typically comprises a dose dial that is rotatable relative to the housing for setting of a dose. The dial extension may further comprise a dose button or trigger button that is depressible in the distal longitudinal direction of the housing for initiating and/or for controlling dispensing or expelling of a dose.

In order to monitor use of an injection device, e.g. for the purpose of surveying the patient's compliance with a prescribed medication schedule such injection devices may be equipped with a detector arrangement operable to detect at least one of a time when an injection takes place and a size of a dose injected or expelled by the injection device. For determining or quantitatively measuring a size of a dose at least one of a rotational and longitudinal displacement of at least one component of the injection device relative to another component of the injection device must be detected and/or measured.

The implementation and embedding of an electronic detector arrangement in a manually operable and/or mechanically implemented injection device is quite challenging, especially when the electronic detector arrangement should be retrofitted into an existing injection device.

It is therefore desirable to provide an injection device with an improved detector arrangement that can be easily applied and embedded with a large variety of different injection devices. The implementation of the detector arrangement should be rather smooth and should be restricted to minor modifications of only one or a few components of the injection device. Moreover, the detector arrangement should be implementable rather cost efficient and should require only a minimum of additional installation space.

SUMMARY

In one aspect the disclosure relates to an injection device for setting and injecting pre-set of user-selectable doses of a medicament. The injection device comprises an elongated housing defining a longitudinal direction. The elongated housing is configured to accommodate a cartridge. The cartridge contains a medicament. The injection device further comprises a detector arrangement that is operable to detect a relative movement between a first element and a second element of the injection device. The first element is subject to a first movement relative to the second element along a first longitudinal direction for setting of a dose. The first element is subject to a second movement relative to the second element along a second longitudinal direction for dispensing of the dose. Here, one of the first movement and the second movement is a helical movement, i.e. the first element is subject to a combined longitudinal and rotational movement with respect to the second element. The other one of the first movement and the second movement is a sliding movement in the longitudinal direction. The sliding movement is a longitudinal sliding movement, wherein the first element is rotationally fixed to the second element. Hence, the sliding movement is not accompanied by a rotation.

Typically, the first longitudinal direction is opposite to the second longitudinal direction. Moreover, a longitudinal component of the first movement is opposite to a longitudinal component of the second movement.

The second element comprises at least one reference element. The reference element may be a dedicated portion of the second element. It may define a positional reference for the first element. The reference element is fixed to the second element. Hence, the reference element is immobile relative to the second element. It may be permanently fixed to the second element.

The first element of the injection device comprises a tubular-shaped surface that is provided with a pattern. The pattern faces towards the at least one reference element. The pattern may be provided on the tubular-shaped surface. It can be attached to the tubular-shaped surface or may be integrated into the tubular-shaped surface. The pattern is a spatial pattern. It may comprise a spatial code and may serve to encode the first element.

The injection device further comprises a detector arrangement. The detector arrangement comprises at least one electric sensor. The electric sensor is operable to detect a positional variation of the pattern relative to the reference element. The electric sensor is further operable to generate at least one electrical signal, typically a sequence of electric signals, in response to the positional variation of the pattern relative to the at least one reference element. Hence, the at least one electric sensor is operable to generate electric signals during and in response to at least one of the first movement and the second movement of the first element relative to the second element.

The at least one electric sensor is arranged on one of the first element and the second element. The at least one electric sensor is operable or configured to directly interact with at least one of the pattern and the reference element. With some examples the at least one electric sensor is operable to detect and/or to determine a direct interaction between the pattern and the reference element. In particular, the at least one electric sensor is operable to detect and/or to determine a degree of a rotation of the first element relative to the second element when the first element is subject to a helical motion relative to the second element. Moreover, the at least one electric sensor may be configured to detect a non-rotational and purely longitudinally sliding displacement of the first element relative to the second element.

With some examples the at least one electric sensor and the respective detector arrangement may be configured or may be operable to detect and/or to measure a longitudinal displacement as well as a rotational displacement of the first element relative to the second element. With some examples the detector arrangement and the at least one electric sensor may be operable to detect and/or to quantitatively measure a rotational displacement and/or a longitudinal displacement between the first element and the second element when the first element is subject to a helical motion relative to the second element.

The detector arrangement and the at least one electric sensor may be configured to measure a rotational displacement and a longitudinal displacement simultaneously. In this way a precision of the detection and measurement can be increased and an error rate of the detection and/or measurement can be decreased.

With a further example the at least one electric sensor is arranged on the first element or on the second element. When the electric sensor is arranged on the second element it may coincide with the reference element or it may constitute the reference element. When the electric sensor is arranged on the first element the at least one electric sensor is typically electrically connected to the pattern of the first element. Then and for detecting and/or measuring a relative displacement of the first element relative to the second element the pattern directly interacts with the reference element of the second element when the first and second elements are subject to at least one of the first movement and the second movement.

Arranging the at least one electric sensor and eventually even the entire detector arrangement on the first element allows and supports a rather easy, straight forward and smooth embedding or integration of the reference element into or on the second element. Here, the reference element may be a passive electronic device or passive electronic structure, such as a bridging contact.

With another example the first movement of the first element relative to the second element is a helical movement. The second movement is a longitudinal sliding movement of the first element relative to the second element during which the first element is rotationally locked to the second element.

With some examples of the injection device a longitudinal displacement of the first element relative to the second element during the first movement is equal in size to a longitudinal displacement of the first element relative to the second element during the second movement.

Typically, the longitudinal component of the first movement is opposite to the longitudinal component of the second movement. If the first element is moved in a longitudinal proximal direction during the first movement it will be moved in the opposite longitudinal direction, i.e. the distal direction during the second movement.

Typically, the longitudinal position of the first element relative to the second element before setting of a dose equals the longitudinal position of the first element relative to the second element after completion of a dose dispensing or dose expelling procedure.

A rotational position, hence a rotational state of the first element relative to the second element before setting of a dose may differ from a rotational state or rotational orientation of the first element relative to the second element after completion of the dose dispensing or dose expelling procedure. This is particularly the case in situations where the helical movement of the first element relative to the second element includes only a fraction of a revolution or a non-integer multiple of a complete revolution of the first element relative to the second element.

With some examples the detector arrangement and the at least one electric sensor is operable to detect and/or to quantitatively measure at least one of the first movement and the second movement irrespective of an initial rotational state or rotational orientation of the first element relative to the second element. A movement detection may start and may end at any conceivable and hence arbitrary rotational position or rotational orientation of the first element relative to the second element.

With some examples the first element and the second element are both of tubular shape. They may be either directly or indirectly mechanically engaged so as to follow a relative helical motion in one longitudinal direction and to follow a relative non-rotational sliding displacement along the other longitudinal direction. The first element and the second element may be arranged in a nested manner. One of the first and second elements may at least in sections circumferentially enclose or radially enclose the other one of the first and the second element.

With some examples the first element is subject to a helical motion along the longitudinal proximal direction relative to the second element for setting of a dose. Then, the first element is subject to a non-rotational sliding displacement relative to the second element along the distal longitudinal direction during dispensing of the dose. With other examples and for setting of the dose the first element is rotationally locked but axially displaceable relative to the second element, typically along the longitudinal proximal direction. For dispensing or expelling of the dose the second element may be subject to a helical motion relative to the second element in the distal direction.

In another example the pattern comprises at least a first pattern portion and a second pattern portion. First and second pattern portions are spatially non-overlapping pattern portions. Hence, the second pattern portion does not overlap with the first pattern portion. On the tubular-shaped surface of the first element, the first pattern portion and the second pattern portion are located next to or adjacent to each other. In this way, the first and the second pattern portions form a spatial pattern allowing to characterize and/or to quantify at least one of a rotational and a longitudinal movement of the pattern relative to the reference.

The at least one electric sensor is capable to distinguish between the first pattern portion and the second pattern portion. Every time one of the first and second pattern portions passes by the at least one electric sensor, the at least one electric sensor is operable to generate a processable electric signal, thus indicating that the pattern is currently subject to a movement relative to the reference element.

With another example the first pattern portion and the second pattern portion distinguish with regard to at least one of the following parameters: electrical conductivity, optical transmissivity, optical reflectivity, magnetic susceptibility or electric susceptibility. The first and second pattern portion may further distinguish by their radial position with regard to a central axis of the tubular-shaped surface. For instance, the first and second patterns may be formed by protrusions or indentations, such as ridges and grooves on the tubular-shaped surface of the first element.

The at least one electric sensor is implemented in accordance to the distinguishing parameters of the first pattern portion and the second pattern portion. If the first and the second pattern portions distinguish by their electrical conductivity the at least one electric sensor is typically capable to measure the electrical conductivity of the pattern and of its respective first and second pattern portions. The at least one electric sensor may comprise at least one electrical contact tap that is configured and operable to get in electrical contact with only one of the first pattern portion and the second pattern portion at a time. Likewise and when the first and second pattern portions distinguish with regard to the optical transmissivity or optical reflectivity the at least one electric sensor typically comprises at least one of a light source and a light detector. Typically, the detector arrangement and the at least one electric sensor comprise a combination of a light source and a light detector, such as a light emitting diode LED and a photodiode.

Accordingly, and when first and second pattern portions distinguish by their magnetic susceptibility or electric susceptibility the at least one electric sensor comprises a respective magnet or dielectric sensor arrangement capable to distinguish between the first pattern portion and the second pattern portion of the pattern of the first element, wherein the first and the second pattern portions feature different magnetizations.

When the first pattern portion and the second pattern portion exhibit different radial positions with regard to a central axis of the tubular-shaped surface the at least one electric sensor may be implemented as a mechanical or electromechanical switch arranged at a predefined radial distance from the central axis. Here, the first and the second pattern portions may distinguish by their radial height. For instance, the first pattern portion may comprise an indentation or groove in the tubular-shaped surface and the second pattern portion may comprise at least one of a protrusion, rib or ridge protruding radially from the tubular-shaped surface of the first element. As at least one of a protrusion or indentation passes by the at least one electric sensor, a respective electromechanically implemented switch may be activated or deactivated thus leading to the generation of a respective electric signal that can be processed for a movement detection and/or for a quantitative measurement of the size of at least one of the first movement and the second movement between the first and the second elements.

According to a further example a longitudinal extension of the pattern is equal to or larger than a maximum longitudinal displacement of the first member relative to the second member. In this way it is ensured, that the first pattern is and remains within a certain range of the reference element even if the first element is subject to a maximum longitudinal displacement relative to the second element. When the reference element is provided with the at least one electric sensor the pattern and the sensor cannot get out of contact or out of interaction even if the first element is subject to a maximum possible longitudinal movement relative to the second element. In this way and for each allowable longitudinal position of the first element relative to the second element at least one of the detector arrangement, the at least one electric sensor and the reference element is and remains in direct interaction with the pattern of the first element.

According to another example the pattern comprises a first pattern section and a second pattern section. The first pattern section and the second pattern section are arranged non-overlapping on the tubular-shaped surface. The second pattern section is separated from the first pattern section in longitudinal direction. In other words, the first pattern section may comprise or form a first longitudinal portion of the pattern and the second pattern section may comprise or form a second longitudinal pattern section non-overlapping with the first longitudinal pattern section.

At least one of the first and the second pattern sections comprises a first pattern portion and a second pattern portion as described above. Even both of the first and the second pattern sections may each comprise at least a first pattern portion and at least a second pattern portion.

For instance, the first pattern section may comprise a first sub-pattern. The second pattern section may comprise a second sub-pattern. First and second sub-patterns may be substantially equal. First and second pattern sections may substantially distinguish. The first and the second pattern section are typically separated in longitudinal direction on the tubular-shaped surface of the first element.

The first and the second pattern sections may serve different detection purposes. The first pattern section may comprise a longitudinal extension that is larger than a longitudinal extension of the second pattern section. Moreover, the second pattern section may be provided or located at an axial end of the first pattern section. The second pattern section may be encircled or surrounded by the first pattern section. With some examples the first pattern section is configured and operable to detect and/or to measure a rotational movement of the first element relative to the second element. The second pattern section may be configured to detect and/or to measure a longitudinal and hence non-rotational movement of the first element relative to the second element.

There may be provided at least one electric sensor to interact with at least one of the first pattern section and the second pattern section. There may be provided at least two electric sensors, one of which configured and operable to exclusively interact with the first pattern section and the other one of which being implemented and exclusively configured to interact with only the second pattern section.

Typically, a transition from the first pattern section towards the second pattern section along the longitudinal direction is detectable by the at least one electric sensor. In this way, the interaction between the least one electric sensor and the first and second pattern sections may serve to detect a particular longitudinal position of the first element relative to the second element, e.g. when the first element returns into an initial configuration or end-of-dose configuration with regard to the second element at the end of a dose dispensing or dose expelling procedure.

In another example the first pattern section comprises a stripe pattern comprising a number of parallel orientated longitudinal stripes. The longitudinal stripes extend parallel to the longitudinal direction. They may hence extend parallel to a central axis of the tubular-shaped surface of the first element. With another example the longitudinal stripes extend at a predefined non-zero angle with regard to the longitudinal direction.

With a stripe pattern comprising a number of parallel oriented longitudinal stripes extending parallel to the longitudinal direction the first pattern section is particularly dedicated and configured to determine and/or to measure a rotational movement of the first element relative to the second element. If the longitudinal stripes extend at a predefined angle with regard to the longitudinal direction, in other words, if the longitudinal stripes of the first pattern section are skewed or slanted with regard to the central axis not only a rotational displacement of the pattern and hence of the first element relative to the second element can be detected and quantitatively measured by means of the at least one electric sensor but also a non-rotating longitudinal sliding movement of the first element relative to the second element can be detected and quantitatively measured, e.g. with only one and the same electric sensor.

The stripe pattern may comprise numerous stripes of equal or different geometry. The stripes may be equiangularly spaced along the circumference of the tubular-shaped surface. In accordance to an angular encoding the stripes of the stripe pattern may also be heterogeneously distributed in tangential direction on the tubular-shaped surface. The stripes of the stripe pattern may also comprise different dimensions.

The position, size, shape and orientation of the stripes of the stripe pattern strongly depend on the specifically implemented encoding scheme. It depends on the number and on the position of the at least one electric sensor. With some examples the number, the size, the geometry and the orientation of the stripes depends on the number, the size and the position or orientation of bridging contacts provided on the second element.

According to a further example the detector arrangement is operable to detect a longitudinal overlapping of the reference element with at least one of the first pattern section and the second pattern section irrespective of a rotational state of the first element relative to the second element. A longitudinal overlapping means that the reference element and at least one of the first pattern section and the second pattern section are located at the same longitudinal position. Here, the reference element and at least one of the first pattern section and the second pattern section may overlap in radial direction with regard to the tubular shape of the pattern.

In particular, the detector arrangement and/or the at least one electric sensor is operable to detect a transition from the first pattern section to the second pattern section and vice versa. In other words, the detector arrangement is configured to detect when the first pattern section initially radially overlapping with the reference element is subject to a longitudinal displacement such that the second pattern section starts to radially overlap with the reference element. A separation or transition between the first and second pattern sections is detectable by the detector arrangement. In this way, a longitudinal or axial end position of the first element relative to the second element can be precisely detected thus indicating to the detector arrangement that e.g. a dose expelling procedure has been completed and that the injection device is in an initial state in which it is ready for a subsequent dose setting and dose injecting procedure. Typically, the detector arrangement is operable and configured to detect a longitudinal sliding displacement of at least one of the first pattern section and the second pattern section relative to the reference element irrespective of a rotational state or rotational orientation of the first element relative to the second element. In effect and with any rotational position of the first element relative to the second element a longitudinal displacement or movement of the first element relative to the second element can be at least detected. In order to achieve such a detection the second pattern section may comprise a pattern or sub-pattern that differs in size and/or geometry from the pattern or sub-pattern of the first pattern section. For instance, the second pattern section may comprise an annular shape enabling a detection of a longitudinal sliding motion or screwing motion of the first element relative to the second element for any available rotational state or rotational orientation of the first element relative to the second element.

In a further example the pattern comprises at least a first pattern portion that is electrically conductive. The pattern comprises at least a second pattern portion that is electrically insulating. Typically, the pattern comprises numerous first pattern portions and numerous second pattern portions. For instance, the pattern comprises a sequence of electrically conductive portions and a sequence of electrically insulating portions. The electrically conductive pattern portions may be electrically separated or galvanically separated from each other through the electrically insulating second pattern portions.

The first pattern portion and the second pattern portion being electrically conductive and electrically insulating, respectively may correspond and represent the above mentioned first and second pattern portions of the pattern that are arranged non-overlapping with respect to each other and that distinguish with regard to their electrical conductivity.

The first and second pattern portions may be arranged alternately along at least one of the first movement and the second movement between the first and the second elements. The first and the second pattern portions may be separated along a circumference or along a tangential direction of the tubular-shaped surface of the first element. The first and the second pattern portions may also be separated along the longitudinal direction of the tubular-shaped surface. The first and the second pattern portions may comprise a stripe pattern with an alternating arrangement of stripes exhibiting at least two different electrical conductivities. The pattern is not limited to a first pattern section and to a second pattern section. There may be provided numerous different pattern sections, such as first, second, third or even more pattern sections that all distinguish from each other e.g. with regard to their electrical conductivity. In this way a higher information density or code density can be provided on the tubular-shaped surface.

With some examples the pattern is provided on an outside surface of the first element. With other examples the pattern is provided on an inside surface of the first element.

The pattern may comprise a binary pattern comprising an information content provided by at least two, namely first and second pattern portions representing a digital 0 or a digital 1, respectively.

The pattern and the at least one electric sensor may be implemented as an incremental or as an absolute quadrature encoder. They may be implemented as a 2-bit gray code. Depending on the number of electric sensors or electric contact taps and depending on the specific implementation of the pattern also other codes, comprising a 3-bit encoding or an n-bit encoding with n being an integer number can be provided.

When the pattern comprises an electrically conductive structure, e.g. when the first pattern portion is electrically conductive it may comprise one of a conductive varnish, a conductive lacquer, a conductive coating or conductive etching. The conductive varnish or conductive lacquer may comprise electrically conductive particles, such as metal particles or carbon black particles. The electrically conductive pattern may also comprise a metal inlay in or on the tubular-shaped surface of the first element. The first element may comprise a thermoplastic material being substantially electrically insulating. In this way only the electrically conductive pattern portions have to be provided on the electrically insulating material of the first element. The electrically conductive first pattern portion may also comprise a sheet metal attached to or embedded in and flush with the tubular-shaped surface of the first element. The at least first electrically conductive pattern portion may be attached or assembled to the tubular-shaped surface by way of insert molding or by way of a two-component injection molding of the first element.

In a further example the detector arrangement comprises at least one electrical contact tap arranged on the second element and operable to alternately connect to the first pattern portion and the second pattern portion of the pattern when the first element is subject to one of the first movement and the second movement relative to the second element. The electrical contact tap may be radially biased so as to frictionally engage with the pattern of the first element. When the pattern is provided on an outer tubular-shaped surface of the first element the at least one electrical contact tap is biased radially inwardly. It is flexible or deformable radially outwardly by the pattern against an inherent restoring force.

When the tubular-shaped surface is an inner surface the at least one electrical contact tap is biased radially outwardly and can be deformed or flexed radially inwardly against a respective restoring force. The electrical contact tap may represent the reference element. Hence, the reference element may comprise the at least one electrical contact tap. The reference element may comprise numerous electrical contact taps arranged and distributed along the outer or inner circumference of the tubular-shaped surface.

With another example the pattern comprises at least a third pattern portion that is electrically conductive, wherein the first pattern portion and the third pattern portion are electrically separated from each other. Hence, the first pattern portion and the third pattern portion are galvanically insulated from each other. The first pattern portion and the third pattern portion can be electrically separated by the second pattern portion that is electrically insulating. Providing at least two different types of electrically conductive pattern portions allows and supports implementation of an n-bit rotary encoder, with n being an integer equal to or larger than 2. When the first pattern portion and the third pattern portion are electrically distinguishable they can be individually and/or separately electrically connectable to the detector arrangement when subject to one of the first and second movement thus enabling e.g. a 3-bit rotary encoder.

With other examples the third pattern portion may be permanently electrically connected to a voltage supply of the detector arrangement. Here, the at least one electric sensor may be electrically connected to the first pattern portion. The rotary encoder may be completed by a bridging contact provided on the second element. The bridging contact may be configured and operable to selectively establish an electric connection between the third pattern portion and the first pattern portion as the first element is subject to a helical or rotational movement relative to the second element. With this example the second element can be void of any active electronic components. It may comprise only passive electrically conducting components, such as electric contact taps or at least one bridging contact.

In another example the detector arrangement and the at least one electric sensor are arranged on the first element. The at least one electric sensor is electrically connected to the first pattern portion. The at least one reference element is arranged on the second element and comprises an electrical bridging contact. The electrical bridging contact is configured to alternately establish and interrupt an electric contact between the first pattern portion and the third pattern portion when the first element is subject to one of the first movement and the second movement relative to the second element.

Typically, the electrical bridging contact extends in a tangential direction with regard to the tubular shape of the first element. The bridging contact may be implemented and operable to establish an electrical contact between the first pattern portion and the third pattern portion, e.g. thereby bridging the second pattern portion located between and/or separating the first pattern portion and the third pattern portion. This electric connection between the first pattern portion and the third pattern portion is typically provided when the first element is in a first rotational position or rotational orientation with regard to the second element. As the second element is subject to a further rotation and arrives at a second rotational state or rotational orientation at least one of the first pattern portion and the third pattern portion loses contact with the electrical bridging contact. In this way, the first pattern portion and the third pattern portion become electrically or galvanically separated.

Since the at least one electric sensor is electrically connected to the first pattern portion a varying electrical contact with the third pattern portion can be detected by the at least one electric sensor as the first element is subject to a rotation relative to the second element. Here, the third pattern portion may also be electrically connected to the at least one electric sensor or to another electric sensor of the detector arrangement. Alternatively, the third pattern portion may be permanently connected to a voltage supply of the detector arrangement. With rotational positions of the first and second elements, in which the first pattern portion is electrically connected to the third pattern portion via the at least one electrical bridging contact the first element is provided with the supply voltage. In other rotational states, wherein the first pattern portion is electrically separated from the third pattern portion the electric sensor connected to the first pattern portion will detect a zero voltage.

Use and implementation of at least one electrical bridging contact is beneficial because the second element can be easily adapted for the implementation and embedding of the detector arrangement. Here, only the geometry of the second element has to be slightly modified in order to receive or to assemble the at least one electrical bridging contact. Insofar, the second element does not require any active electric or electronic components but requires only a passive electrically conductive structure.

With another example the electrical bridging contact comprises a first electrical contact tap and a second electrical contact tap. The first electrical contact tap and the second electrical contact taps are electrically connected. The first electrical contact tap and the second electrical contact tap are spatially separated from each other along a first separation direction parallel to a distance between the first pattern portion and the third pattern portion. The magnitude of spatial separation between the first electrical contact tap and the second electrical contact tap is typically larger than a size or width of at least one of the first pattern portion and the third pattern portion as seen along the first separation direction.

Typically, the spatial separation between the first electrical contact tap and the second electrical contact tap is at least equal to or larger than the size or extension of the second pattern portion located between the first pattern portion and the third pattern portion as seen along the first separation direction. In this way it is ensured, that at least with one rotational state or rotational orientation of the first element relative to the second element the first pattern portion is electrically connected to the third pattern portion via the electrical bridging contact, namely when the first electrical contact tap is in electrical connection with the first pattern portion and the second electrical contact tap is in electrical connection with the third pattern portion.

With another example the first separation direction extends substantially parallel to an imaginary shortest connection between the first pattern portion and the third pattern portion. For instance, if the first and the second pattern portions are portions of a stripe pattern the first separation direction extends substantially perpendicular to the longitudinal extension of the stripes of the pattern.

According to a further example the electrical bridging contact comprises a third electrical contact tap spatially separated from at least one of the first electrical contact tap and the second electrical contact tap along a second separation direction that is non-parallel to the first separation direction. With some examples the second separation direction extends substantially perpendicular to the first separation direction. If the pattern on the first element comprises a longitudinal stripe pattern the first and second electrical contact taps are particularly configured to alternately engage or to alternately contact the alternating stripes as the first element is subject to a rotation or helical movement relative to the second element.

Typically, the first and the second electrical contact taps are only displaceable relative to the first element in the region of the first pattern section. Moreover, the first pattern section may be entirely provided with a stripe pattern comprising at least one first, second and at least one third pattern portion.

The third electrical contact tap of the electrical bridging contact may be located offset from at least one or from both of the first electrical contact tap and the second electrical contact tap along the longitudinal direction. In this way and as the first element is subject to a longitudinal displacement relative to the second element the third electrical contact tap may reach into or onto the second pattern section. The second pattern section may be separated from the first pattern section along the longitudinal direction. The second pattern section may be out of reach for the first and the second electrical contact taps of the electrical bridging contact but it may be engageable with only the third electrical contact tap of the electrical bridging contact. In this way the interaction of the third electrical bridging contact with the second pattern section may be an indicator that a longitudinal end position, e.g. a zero dose configuration or end-of-dose configuration of the injection device has been reached.

Accordingly and in another example the third bridging contact is configured to get in contact with the second pattern section when the first element and the second element return into an initial relative position after completion of the dispensing of the dose. In this way, the mutual engagement or contact between the third bridging contact and the second pattern section provides a zero dose indicator thus indicating to the detector arrangement, that the end of a dose dispensing or expelling procedure has been reached.

With further examples the injection device comprises two or more electrical bridging contacts that are distributed along the tubular circumference of the first element. The two or more electrical bridging contacts may be located at the same longitudinal position on the second element. They may be equiangularly or equidistantly arranged along the circumference or along the tangential direction of the tubular-shaped surface of the first element.

Typically, also the second element is of tubular shape. Accordingly, the two or more electrical bridging contacts can be separated from each other along the circumference or tangential direction of the tubular-shaped second element. The two or more electrical bridging contacts can be implemented identically. Hence, a first electrical bridging contact has the same shape and geometry compared to a second electrical bridging contact. The two or more electrical bridging contacts can be also asymmetrically arranged along the circumference of the second element. Hence, a distance or angular distance between a first and a second electrical bridging contact may differ from a distance or angular distance between the second and a third electrical bridging contact. The geometric arrangement of the two or more electrical bridging contacts depends on the encoding of the pattern on the first element.

With another example the two or more electrical bridging contacts and the first and the third pattern portions are arranged such, that in any available rotational position of the first element relative to the second element at least one of the first pattern portions is electrically connected to at least one of the third pattern portion via the at least one of the bridging contacts. In this way, at least one of the first pattern portions is at a supply voltage if the at least one third pattern portion is connected to a voltage supply. In this way, an unequivocal electrical signal can be provided for each available rotational position of the first element relative to the second element.

In another example the electrical bridging contact comprises a body made of sheet metal and further comprising at least one flexible arm. At least one of the first electrical contact tap and the second electrical contact tap is arranged at a free end of the at least one flexible arm. The electrical bridging contact may comprise numerous flexible arms, such as a first flexible arm, a second flexible arm and optionally also a third flexible arm. Typically, the first electrical contact tap is located at or on a free end of the first flexible arm of the electrical bridging contact. The second electrical contact tap is arranged or located at a free end of the second flexible arm of the electrical bridging contact. The same may be valid for an optional third electrical contact tap. Also the third electrical contact tap can be provided and arranged at or on a free end of a third flexible arm of the electrical bridging contact.

The electrical bridging contact can be fastened to or can be embedded in the second element. For instance, the electrical bridging contact is insert-molded in or on the second element, which may comprise an injection molded plastic component. Typically, the at least one flexible arm of the electrical bridging contact may be radially biased or pre-tensed towards the tubular-shaped surface of the first element. This ensures a non-interrupting mechanical contact between the at least one arm and/or of the respective electrical contact tap with the pattern on the tubular-shaped surface.

The at least first electrical contact tap may protrude from the at least first flexible arm of the electrical bridging contact. It may comprise an embossed dome-shaped or spherical structure integrally formed in the sheet metal and protruding from the flexible arm towards the tubular-shaped surface of the first element. The electrical bridging contact may be manufactured by metal pressing. It may comprise stainless steel. The electrical contact taps may comprise a dome-shaped embossed pin in the flexible arm exhibiting only a rather low degree of static or dynamic friction with regard to the pattern.

The at least one flexible arm may comprise or form a cantilever member ensuring a good radial contact pressure between the pattern and the electrical bridging contact. A preload and/or the radial deformation of the at least one flexible arm should be at least in a range of manufacturing and/or assembly tolerances of the injection device. In this way, eventual manufacturing or assembly tolerances can be easily compensated.

In a further example the injection device comprises at least one cleaning pad arranged in or on the second element at a distance from the at least one electrical contact tap along at least one of the first movement and the second movement. The cleaning pad is typically in frictional engagement with the tubular-shaped surface of the first element. The at least one cleaning pad is in mechanical and frictional engagement with those portions of the pattern of the tubular-shaped surface that will get in electrical contact with at least one electrical contact tap as the first element is subject to one of the first movement and the second movement relative to the second element.

In this way, those portions of the tubular-shaped surface that will get in electrical contact with the at least one electrical contact tap will be cleaned. In this way, a rather long-lasting and reliable electrical contact between the electrically conductive pattern and the at least one electrical contact tap can be established and maintained. Moreover, particles, such as dust particles that may accumulate on the tubular-shaped surface can be wiped away. Their potentially detrimental effect on the electrical contact between the at least one electrical contact tap and the electrically conductive pattern can be thus reduced. Moreover, by cleaning the tubular-shaped surface abrasion or wear induced by the at least one electrical contact tap sliding along the pattern can be effectively reduced.

Typically and in another example the cleaning pad comprises one of an elastomeric material and a textile material. The cleaning pad faces towards the pattern. The cleaning pad is configured to frictionally engage with the first element when the first element is subject to one of the first movement and the second movement relative to the second element. An elastomeric or textile material of the cleaning pad is of benefit for a long-lasting and gently cleaning effect of the respective cleaning pad. With a further example the cleaning pad is one of elastically deformable or pivotable with regards to the longitudinal direction as a deformation axis or pivot axis.

Comparable to a wiper blade of a windscreen wiper the cleaning pad may comprise a narrowing or pointed geometry towards the first element. It may be further pivotable or elastically deformable under the effect of the first element rotating relative to the second element. For instance and when the first element is subject to a helical motion along a first sense of rotation the cleaning pad may be automatically pivoted so as to enlarge its contact surface with the tubular-shaped surface. As the helical motion stops the at least one cleaning pad may return into an initial configuration, in which it has only a comparatively small contact area or contact surface with the tubular-shaped surface of the first element. In this way, abrasion or wear of the tubular-shaped surface and of the pattern provided thereon can be reduced.

With another example a length of a longitudinal movement of the first element relative to the second element during the first movement is identical to a length of a longitudinal movement of the first element relative to the second element during the second movement. At least one of the contact taps is at a first rotational position relative to the pattern before the first element and the second element are subject to the first movement. When the helical movement of the first element relative to the second element during one of the first movement and the second movement comprises a non-integer multiple rotation of the first element relative to the second element the at least one of the contact taps is at a second rotational position after a completion of the second movement. Here, the second rotational position and the first rotational position differ.

Accordingly, in the first rotational position a first portion of the pattern is in contact with the at least one contact tap. In the second rotational position another and hence a different portion of the pattern is in contact with the at least one contact tap. This configuration is rather beneficial for reducing abrasion or wear of the pattern on the tubular-shaped surface of the first element. The at least one or numerous contact taps of the detector arrangement and/or of the reference element may be in permanent mechanical contact with the tubular-shaped surface of the first element. Since the first element is only subject to a rotation during the first movement and since a dose setting including an integer or integer multiple rotation of the first element relative to the second element may represent only an exceptional and rather rare case the tubular-shaped surface is rather homogeneously stressed in terms of friction with the at least one contact tap.

With another example the detector arrangement is arranged on the second element. Here, the at least one electric sensor comprises at least a first electrical contact tap arranged on the second element. The first electrical contact tap is configured to alternately get in mechanical and electrical contact with the first pattern portion and the second pattern portion when the first element is subject to one of the first movement and the second movement relative to the second element. With such a configuration, a binary 2-bit gray code rotary encoder can be implemented. Typically, the electric sensor comprises at least one first electrical contact tap and a second electrical contact tap distributed or arranged along the tubular circumference of the first element along a first separation direction.

The distance between neighboring electrical contact taps and the distance between neighboring first and second pattern portions may be substantially equal. Moreover, the periodicity of the arrangement of numerous electrical contact taps and the periodicity of the pattern may be substantially equal. With such a configuration at least two or all available sensor taps may simultaneously produce or modify an electrical signal. Here, a second sensor tab may provide a backup for a first sensor tab and the detector arrangement comprises a respective redundancy and failure safety.

With other examples the spatial or angular distance between neighboring contact taps and neighboring first and second pattern portions mutually differ. In this way the individual contact taps of the electric sensor provide different and/or alternating electrical signals as the first element is subject to at least one of the first movement and the second movement relative to the second element, in particular when the first element is subject to a rotation relative to the second element during the helical movement.

With another example the distance between neighboring contact taps along the first separation direction is smaller than a spatial extension of at least one of the first pattern portion and the second pattern portion along the first separation direction. In this way, it can be achieved, that there will be at least some rotational states of the first element relative to the second element, where not only one but two contact taps will be electrically connected with one and the same pattern portion. This may be beneficial for generating a binary signal, such as to implement a 2-bit gray code or an incremental quadrature encoder.

With all examples as described herein the first and the second elements may be implemented as arbitrary components of an injection device, typically of a pen-type injection device that are subject to the first movement relative to each other during setting of a dose and that are subject to the second movement relative to each other during dispensing or expelling of the dose. The first and the second element may be located inside the housing of the injection device. They may be invisible from outside the injection device. The first and the second element may be implemented as components of a drive mechanism of an injection device. The first and the second element may be typically indirectly mechanically engaged so as to enable a helical motion in one longitudinal direction and to enable a rotationally locked sliding displacement along the opposite longitudinal direction. The drive mechanism typically comprises a clutch mechanically engaged with the first element and with the second element. The clutch comprises at least two configurations. In one configuration of the clutch the first element is displaceable relative to the second element along a helical direction. In a second configuration of the clutch the first element is displaceable relative to the second element along a non-rotational and longitudinal sliding movement.

Typically, the first element is subject to a helical and proximally directed movement relative to the second element during setting of a dose and the first element is subject to a non-rotational sliding displacement relative to the second element during dispensing or expelling of the dose.

Typically, the longitudinal or axial position of the first element relative to the second element before setting of a dose is identical to the axial or longitudinal position of the first element relative to the second element after dispensing or expelling of the dose.

With other examples, the second element is a tubular-shaped housing component of the injection device. The second element may comprise a proximal housing component configured to receive a dial extension and/or the drive mechanism of the injection device. Here, the first element may belong to a dial extension of the injection device. The first element may comprise a tubular sleeve carrying and/or mechanically supporting a dose dial. Alternatively, the first element may be integrally formed with a dose dial. Typically and when subject to the first movement relative to the second element the first element protrudes in proximal direction from the second element.

Only by way of example, the injection device and the detector arrangement as described herein is suitable for implementation into a drug delivery device as disclosed in WO 2010/052275 A2. Here, a cylindrical housing sleeve of a dosing assembly may represent the second element according to the present disclosure and a dosage selector may represent the first element pursuant to the present disclosure. In this document the dosage selector is subject to a proximally directed helical motion for setting of a dose and is subject to a non-rotating distally directed movement relative to the housing sleeve for dispensing of a dose.

Residual parts of the injection device that are required for setting and dispensing of a dose of the medicament from the cartridge are not illustrated in greater detail here. They may be implemented identically or in the same way as described in document WO 2010/052275 A2, the entirety of which is herein incorporated by reference.

In another aspect the disclosure relates to a detector arrangement operable to detect a relative movement between a first element and a second element of an injection device. The detector arrangement comprises at least one electric sensor and at least one reference element. One of the electric sensor and the reference element is arranged on the first element and the other one of the electric sensor and the reference element is arranged on the second element. The first element is moveable relative to the second element for setting and for dispensing or expelling of a dose of the medicament contained in a cartridge being arranged inside the injection device.

During and for setting of a dose of the medicament the first element is subject to a first movement relative to the second element. The first element is subject to a second movement relative to the second element for dispensing of a dose. One of the first movement and the second movement is a helical movement and the other one of the first movement and the second movement is a non-rotational sliding movement in longitudinal direction. Typically, the first element and the second element are coaxially arranged. The first and/or the second element may comprise a tubular-shaped elongated body. Typically, the first element and the second element are both of tubular geometry. They may be displaceable in a telescopic manner. Typically, the first movement is the helical movement during which the first element is longitudinally and rotationally displaceable relative to the second element in a longitudinal proximal direction. During the second movement the first element is non-rotationally longitudinally displaceable in distal direction relative to the second element.

The detector arrangement further comprises a pattern provided or arranged on a tubular-shaped surface of the first element. The pattern is subject to a longitudinal or helical movement relative to the reference element during at least one of the first movement and the second movement of the first element relative to the second element. The detector arrangement comprises at least one electric sensor that is operable to generate electric signals in response to a positional variation of the pattern relative to the reference element.

The detector arrangement is suitable for integration or embedding in various injection devices, typically into hand-held pen-type injection devices. Such injection devices may be configured as reusable devices, wherein the cartridge containing the medicament is replaceable. The detector arrangement is also suitable for disposable injection devices intended to be discarded entirely when the medicament provided in the cartridge has been used up or should not longer be used.

The detector arrangement, in particular the electric sensor and the pattern thereof may comprise any of the features mentioned above with regard to the injection device.

In the present context the term 'distal' or 'distal end' relates to an end of the injection device that faces towards an injection site of a person or of an animal. The term 'proximal' or 'proximal end' relates to an opposite end of the injection device, which is furthest away from an injection site of a person or of an animal.

The term "drug" or "medicament", as used herein, means a pharmaceutical formulation containing at least one pharmaceutically active compound,
  wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound,
  wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis,
  wherein in a further embodiment the pharmaceutically active compound comprises at least one peptide for the treatment and/or prophylaxis of diabetes mellitus or complications associated with diabetes mellitus such as diabetic retinopathy,
  wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by Δ and λ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the embodiments disclosed herein without departing from the scope of the disclosure. Further, it is to be noted, that any reference numerals used in the appended claims are not to be construed as limiting the scope of the disclosure.

BRIEF DESCRIPTION OF THE FIGURES

In the following, numerous examples of the drug delivery device, the drug delivery system and of a method of adjusting at least one expelling or dispensing parameter of a drug delivery device are described in detail by making reference to the drawings, in which:

FIG. 23 shows the configuration of FIG. 22, wherein the first element is in a second longitudinal position relative to the second element, FIG. 24 shows the example of FIG. 16 with the first element being close to a zero dose longitudinal position, FIG. 25 shows the arrangement of FIG. 24 wherein the first element is in the zero dose longitudinal position relative to the second element.

DETAILED DESCRIPTION

Figure 1:
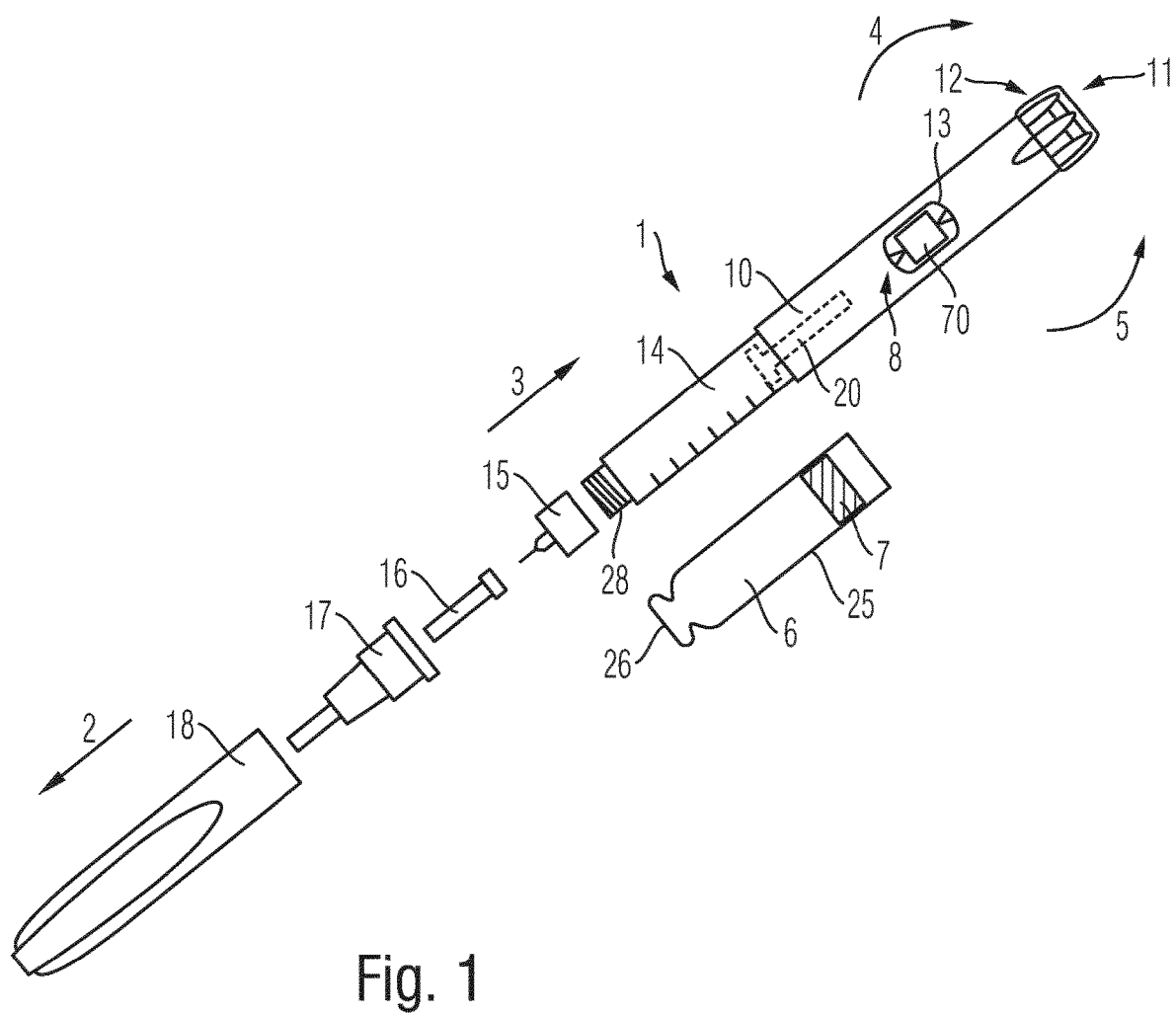
FIG. 1 schematically shows an injection device of pen injector type.

In FIG. 1 an example of an injection device is schematically illustrated. The injection device 1 may comprise a pre-filled disposable injection device. The injection device 1 comprises a housing 10 to which an injection needle 15 can be affixed. The injection needle 15 is protected by an inner needle cap 16 and either an outer needle cap 17 or a protective cap 18 that is configured to enclose and to protect a distal section of the housing 10 of the injection device 1. The housing 10 may comprise and form a main housing part configured to accommodate a drive mechanism 8. The injection device 1 may further comprise a distal housing component denoted as cartridge holder 14. The cartridge holder 14 may be permanently or releasably connected to the main housing 10. The cartridge holder 14 is typically configured to accommodate a cartridge 6 that is filled with a liquid medicament. The cartridge 6 comprises a cylindrically-shaped or tubular-shaped barrel 25 sealed in proximal direction 3 by means of a bung 7 located inside the barrel 25. The bung 7 is displaceable relative to the barrel 25 of the cartridge 6 in a distal direction 2 by means of a piston rod 20. A distal end of the cartridge 6 is sealed by a pierceable seal 26 configured as a septum and being pierceable by a proximally directed tipped end of the injection needle 15. The cartridge holder 14 comprises a threaded socket 28 at its distal end to threadedly engage with a correspondingly threaded portion of the injection needle 15. By attaching the injection needle 15 to the distal end of the cartridge holder 14 the seal 26 of the cartridge 6 is penetrated thereby establishing a fluid transferring access to the interior of the cartridge 6.

When the injection device 1 is configured to administer e.g. human insulin, the dosage set by a dial member 12 at a proximal end of the injection device 1 may be displayed in so-called international units (IU, wherein 1 IU is the biological equivalent of about 45.5 μg of pure crystalline insulin (1/22 mg).

As shown further in FIG. 1, the housing 10 comprises a dosage window 13 that may be in the form of an aperture in the housing 10. The dosage window 13 permits a user to view a limited portion of a number sleeve that is configured to move when the dose member 12, e.g. in form of the dial member is turned, to provide a visual indication of a currently set dose. The dose member may be rotated on a helical path with respect to the housing 10 when turned during setting and/or dispensing or expelling of a dose. During and for setting of a dose the dose dial 12 is typically rotated clockwise, in a dose incrementing direction 4. If a dose actually set should be too large, the dose dial 12 can be also rotated in the opposite sense, hence in a dose decrementing direction 5.

Figure 2:
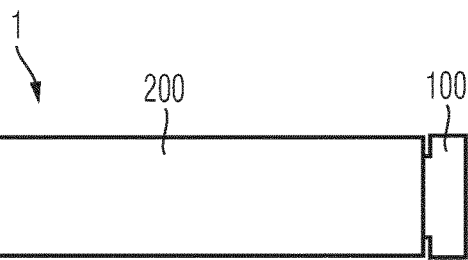
FIG. 2 is a schematic illustration of the first and second elements of the injection device prior to a dose setting procedure.
Figure 3:
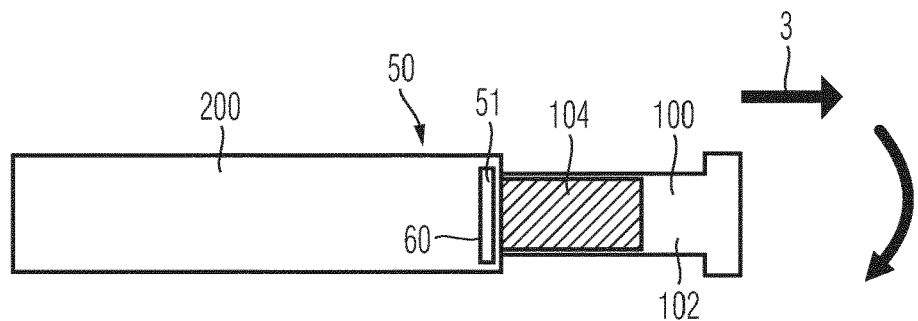
FIG. 3 is a schematic illustration of the first and second elements during or after setting of a dose.
Figure 4:
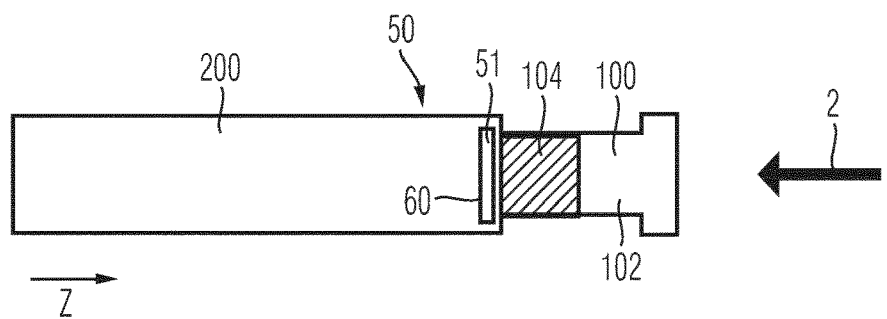
FIG. 4 shows the first and the second elements during dispensing or expelling of a dose.

FIGS. 2-4 are illustrative of one example of a detector arrangement 50 operable to detect and to quantitatively measure a relative movement between a first element 100 and a second element 200 of an injection device 1. Here, the first element 100 is subject to a first movement relative to the second element 200 as illustrated in FIG. 3. The first movement is a helical movement, hence a combined rotational and longitudinal movement of the first element 100 relative to the second element 200. During the first movement the first element 100 may be subject to a clockwise rotational movement relative to the second element 200. Concurrently it may be subject to a longitudinal movement in a proximal direction 3. During setting of a dose the first element 100 is subject to the first movement relative to the second element 200 as illustrated in FIG. 3.

The first element 100 is also subject to a second movement relative to the second element 200. Here, the second movement is a longitudinal movement of the first element 100 relative to the second element 200 along the second longitudinal direction, hence in distal direction 2. The second movement is a sliding movement of the first element 100 relative to the second element 200, wherein the first element 100 is rotationally locked to the second element 200. Hence, during the second movement the first element 100 cannot rotate relative to the second element 200. The second element 200 is provided with at least one reference element 60. The reference element 60 is fixed to the second element 200. It may be arranged at a proximal end of the second element 200.

The detector arrangement 50 comprises at least one electric sensor 51 and a tubular-shaped surface 102. The tubular-shaped surface 102 is provided on the first element 100. Typically, the first element 100 is also of tubular shape. The first element 100 may comprise a sleeve, such as a dose dial sleeve or dosage sleeve operably connected or integrally formed with a dose dial 12 as illustrated in FIG. 1. The detector arrangement 50 comprises at least one electric sensor 51 that is operable to generate electric signals in response to a positional variation of the pattern 104 relative to the reference element 60 during at least one of the first movement and the second movement of the first element 100 relative to the second element 200. The reference element 60 is arranged on or integrated into the second element 200. The at least one electric sensor 51 may coincide with the reference element 60. With other examples the at least one electric sensor 51 may be integrated into or arranged on the first element 100. Then, the reference element 60 can be a passive electric or electronic element operable to interact with the at least one electric sensor 51 located on the first element 100.

The pattern 104 is designed and configured to interact with the at least one electric sensor 51 in such a way that a movement of the pattern 104 according to at least one of the first movement and the second movement is detectable and/or quantitatively measurable by the at least one electric sensor. As the structure of the pattern 104 changes due to a movement of the pattern 104 relative to the reference element 60 the at least one electric sensor 51 generates an electric signal or modifies an electric signal, which electric signal is processable by the detector arrangement 50 in order to detect and/or to quantitatively measure at least one of the type of the movement, the size of the movement, the position and orientation of the first element relative to the second element.

The at least one electric sensor 51 is particularly operable to directly detect and/or to directly quantitatively measure a positional variation of the pattern 104 relative to the at least one reference element 60. Hence, the at least one electric sensor 51 interacts with an interface between the first element 100 and the second element 200.

The at least one electric sensor 51 is operable to detect and/or to quantitatively measure at least one of the helical movement and the sliding movement of the first element 100 relative to the second element 200. The electric sensor 51 may be further configured to detect and/or to quantitatively measure both, a rotational movement and a longitudinal movement of the pattern 100 relative to the reference element 60.

In FIGS. 2-4 the tubular-shaped surface 102 is an outer surface of the tubular-shaped first element 100. The second element 200 may be implemented as another tubular-shaped element. Both, the first element 100 and the second element 200 may comprise a tubular shape. They may be arranged in a nested, hence telescopic configuration. During dose setting the overall longitudinal extension of the assembly of the first element 100 and the second element 200 is larger than at the end of a dose dispensing procedure as illustrated in FIG. 2. The second element 200 is typically a hollow tubular-shaped sleeve. The at least one reference element 60 is typically arranged at an inside side wall of the sleeve of the second element 200. In the same way, also the at least one electric sensor 51 is arranged at a radially inwardly facing portion of the second element 200. The free inner diameter of the second element 200 is larger than an outer diameter of the first element 100. Hence, the first element 100 is longitudinally displaceable inside the second element 200.

Figure 5:
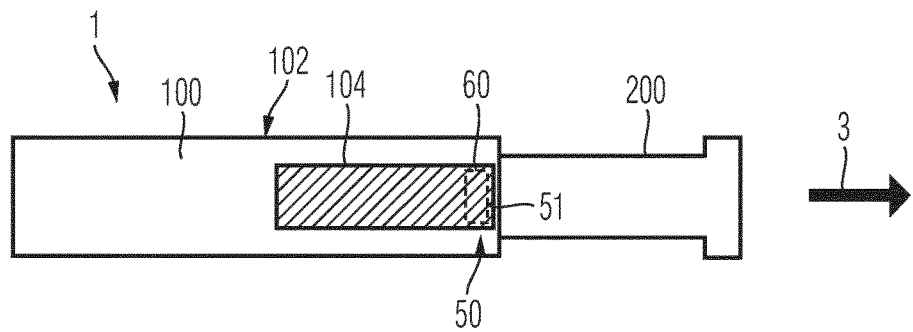
FIG. 5 shows another example of the first and the second elements during or after setting of a dose and FIG. 6 is illustrative of the example of FIG. 5 during dispensing of the dose.
Figure 6:
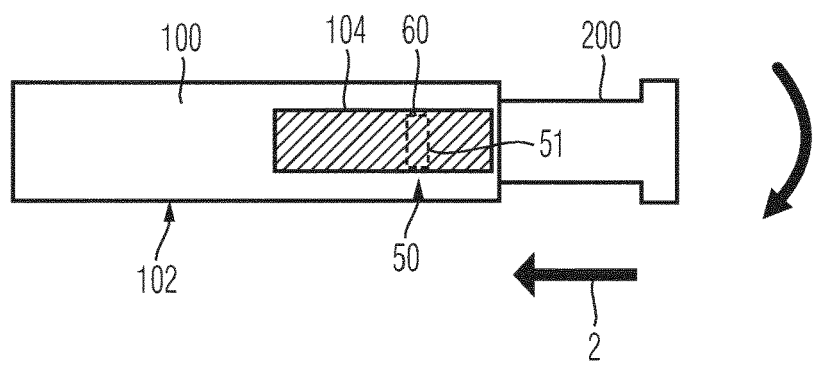

In the example of FIGS. 5 and 6 the first element 100 is again provided with the tubular-shaped surface 102 comprising the pattern 104. But here, the tubular-shaped surface 102 is an inside facing surface of the hollow-shaped first element 100. The second element 200 is longitudinally displaceable in a non-rotational manner relative to the first element 100 during setting of a dose as illustrated in FIG. 5. Here, the second element 200 is subject to a proximally directed longitudinal sliding motion relative to the first element 100 during and/or for setting of the dose. The reference 60 and the at least one electric sensor 51 is located and arranged on an outside circumference of the second element 200. The second element 200 may comprise a tubular shape. It comprises an outer diameter that is smaller than a free inner diameter of the first element 100.

For dispensing of a dose or during dispensing of a dose the second element 200 is subject to a helical movement with a longitudinal displacing component in the longitudinal distal direction 2. Here, the reference element 60 and the at least one electric sensor 51 are subject to a combined rotational and longitudinal movement relative to the pattern 104 and hence relative to the first element 100. As illustrated in FIGS. 5 and 6 the first movement as shown in FIG. 5 is a sliding movement of the first element 100 relative to the second element 200 along the longitudinal proximal direction 3 while the first element 100 and the second element 200 are rotationally locked.

The second movement as illustrated in FIG. 6 is a helical movement of the second element 200 relative to the first element 100 with a longitudinal displacement in distal direction 2. It should be noted, that the tubular-shaped pattern 104 may cover the entirety of the inner circumference of the hollow-shaped first element 100. In this way and for any available rotational state of the second element 200 relative to the first element 100 there will be a defined relative and distinguishable position or orientation of the pattern 104 relative to the at least one reference element 60 or electric sensor 51.

Figure 7:
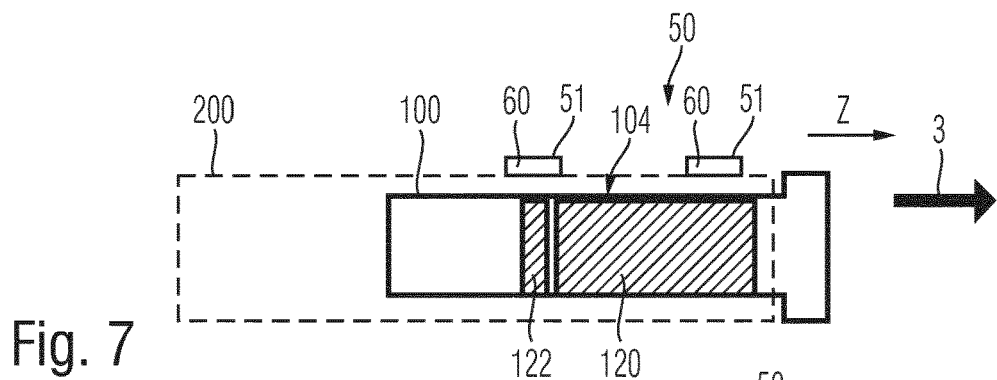
FIG. 7 is illustrative of the first element in relation to the reference element.

In FIG. 7 another example of a detector arrangement 50 is illustrated. Here, the second element 200 is provided with two reference elements 60 that are arranged on or in the second element 200 at a predefined longitudinal distance from each other. In FIG. 7 the second element is only shown with dashed lines when the first element 100 is in a zero dose configuration, e.g. at the end of a dose dispensing procedure. Here, the first element 100 is in a distal most position relative to the second element 200.

As illustrated in FIG. 7 the pattern 104 comprises a longitudinal extension that matches substantially with the longitudinal distance between the first and the second reference elements 60, each of which overlapping or coinciding with a first and a second electric sensor 51. In the initial configuration as illustrated in FIG. 7, one of the reference elements 60 and the electric sensor 51 is located at a proximal end of the pattern 104, wherein the other one of the reference element 60 and the electric sensor 51 is located near or close to a distal end of the pattern 104.

As the first element 100 becomes subject to the first movement and when the first element 100 is displaced in proximal direction 3 relative to the second element 200 the pattern 104 starts to separate from the distally located reference element 60 and from the distally located electric sensor 51. Accordingly, the movement of the first element 100 relative to the second element 200 is detected and/or quantitatively measured only by way of the proximally located reference element 60 and the respective proximally located electric sensor 51.

As the first element 100 approaches the zero dose configuration as illustrated in FIG. 7 at the end of a dose dispensing procedure the pattern 104, typically the distal portion of the pattern 104 returns into the area of coverage of the distally located reference element 60 and/or of the distally located electric sensor 51. The approaching and/or arriving of the first element 100 in the zero dose configuration is hence separately detectable by the distally located electric sensor 51. Here, the distally located electric sensor 51 may be limited to provide the function of a switch configured to indicate to the detector arrangement 50 that the zero dose configuration has been reached. The other and hence the proximally located electric sensor 51 may be thus configured and operable to detect and/or to quantitatively measure a distance or an angular distance the first element 100 has been moved during at least one of the first movement and the second movement relative to the second element 200.

As further illustrated in FIG. 7 the pattern 104 may comprise a first pattern section 120 and a second pattern section 122. The first and the second pattern sections 120, 122 are arranged non-overlapping on the tubular-shaped surface 102 of the first element 100. The second pattern section 122 is separated from the first pattern section 120 at least on longitudinal direction.

Typically, the second pattern section 122 may comprise an annular shape. It may be invariant with regard to the rotational state or orientation of the first element 100 relative to the second element 200. It may be particularly configured to detect a predefined longitudinal position of the first element 100 relative to the second element 200. Contrary to that the first pattern section 120 may be configured and designed to support and allow a detection and/or a quantitative measuring of a degree of rotation or of a longitudinal displacement of the pattern 104 relative to the reference element 60. With some examples the interaction of the first pattern section 120 with the reference element 60 and the at least one electric sensor 51 is operable to exclusively detect and/or to quantitatively measure a degree of rotation of the first element 100 relative to the second element 200.

Figure 8:
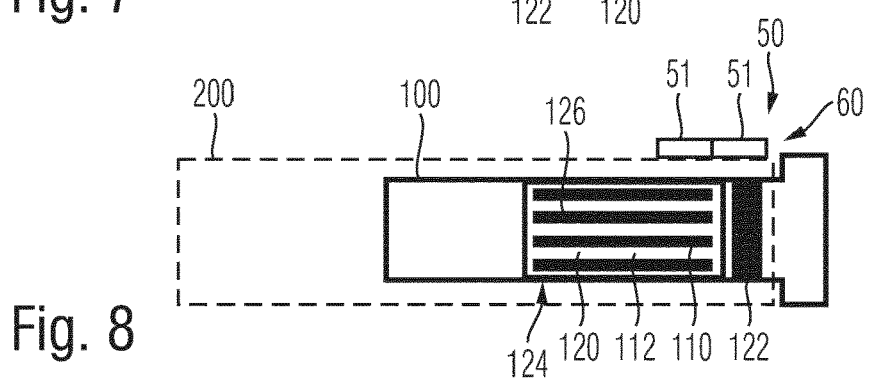
FIG. 8 shows another example of the first element.
Figure 9:
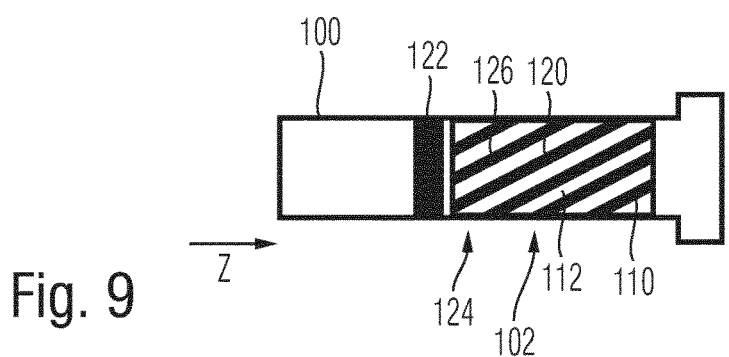
FIG. 9 shows a further example of the first tubular-shaped element.

For this, the first pattern section 120 may be invariant in longitudinal direction (z) hence, a longitudinal and non-rotational displacement of the first element 100 relative to the second element 200 may not generate an electric signal with the at least one electric sensor 51. This is particularly the case, wherein the pattern 104, in particular the first pattern section 120 comprises a stripe pattern 124 as illustrated in FIG. 8. The stripe pattern 124 may comprise numerous longitudinal stripes 126 extending parallel to the longitudinal direction or parallel to the elongation of the tubular-shaped first element 100. With another example as illustrated in FIG. 9, the first pattern section 120 also comprises a stripe pattern 124. But there, the longitudinal stripes 126 extend at a predefined angle with regard to the longitudinal direction (z).

The angle of the longitudinal stripes with regard to the longitudinal direction may differ from a lead of the helical movement between the first element 100 and the second element 200. In this case and as the first element 100 is subject to the helical movement relative to the second element 200 the at least one electric sensor will be operable to generate varying electric signals being indicative of the degree of the rotational displacement of the first element 100 relative to the second element 200. With the angled stripe pattern as illustrated in FIG. 9 varying electric signals will be also generated when the first element 100 is subject to the longitudinal non-rotational sliding movement relative to the second element 200.

As illustrated in FIGS. 8 and 9 the pattern 104 comprises the first pattern section 120 that is particularly configured and dedicated to the detection and/or quantitative measuring of a degree of rotation of the first element 100 relative to the second element 200. In FIG. 8, the second patter section 122 is located adjacent to a proximal end of the first pattern section 120. In FIG. 9, the second pattern section 122 is located adjacent to a distal end of the first pattern section 120. In the configuration of FIG. 8 and when the second pattern section 122 is close to or adjacent to a proximal end of the first pattern section 120 respective electric sensors 51 particularly configured for the detection and/or measuring of a rotational movement and a longitudinal movement, can be arranged close to each other. Moreover, separate electric sensors 51 could be combined in only one electric sensor 51 and may be integrated into only one reference element 60 located near or at a proximal end of the second element 200.

There is generally no restriction with regard to the physical or technical interaction between the pattern 104 and the at least one electric sensor 51.

Typically, the pattern 104 comprises at least a first pattern portion 110 and at least a second pattern portion 112. First and second pattern portions 110, 112 are arranged non-overlapping on the tubular-shaped surface 102 of the first element 100. The first pattern portion 110 and the second pattern portion 112 distinguish with regards to at least one of the following parameters: electrical conductivity, optical transmissivity, optical reflectivity, magnetic susceptibility or electric susceptibility. Moreover, the first and the second pattern portions 110, 112 may also distinguish from each other with regard to a radial position with regard to a central axis of the tubular-shaped surface 102 or with regards to a central axis of the tubular-shaped first element 100. For instance, the first pattern portion 110 may comprise one or several radial protrusions and the second pattern portion 112 may comprise one or several radial indentations. The radial protrusions and indentations may be provided on an outer tubular-shaped surface 102 of the first element 100 or on an inner tubular-shaped surface of the first element depending on the specific implementation of the injection device 1 and the detector arrangement 50.

The at least one electric sensor 51 is configured to communicate or to interact with the first and the second pattern portions 110, 112. Hence, the at least one electric sensor 51 is configured to distinguish between a first pattern portion 110 and a second pattern portion 112 if the respective pattern portions 110, 112 are in a defined area of coverage of the at least one electric sensor 51. When the first pattern portion 110 distinguishes by its electrical conductivity from the second pattern portion 112, the at least one electric sensor 51 may comprise an electric contact tap 52 thus allowing to generate varying electric signals as first and second pattern portions 110, 112 pass by the at least one electric sensor 51. When the first and the second pattern portions 110, 112 comprise one of a different optical transmissivity or optical reflectivity or when first and second pattern portions 110, 112 comprise different colors or distinguish in term of brightness the at least one electric sensor 51 may be implemented as an optical sensor, such as a photodiode operable to distinguish between pattern portions 110, 112 featuring different optical transmissivity, different optical reflectivity or different color or different brightness. When the first and the second pattern portions 110, 112 exhibit different magnetic susceptibility the at least one electric sensor may be implemented as a magnetic sensor. It may comprise a Hall sensing element or a magnetically sensitive electronic structure. The same is valid for a combination of the at least one electric sensor with the pattern wherein the first and the second pattern portions 110, 112 exhibit different electric susceptibility.

Figure 38:
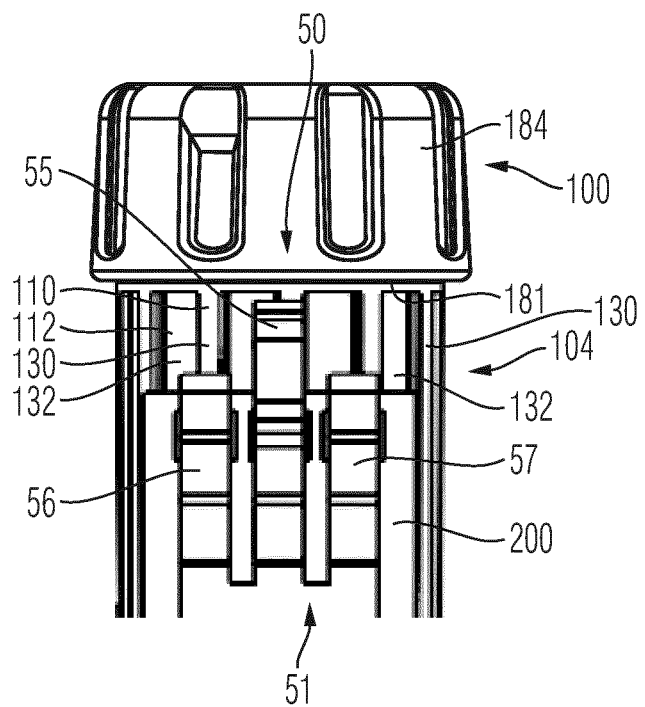
FIG. 38 is illustrative of a further example of the detector arrangement.

When the first and the second pattern portions 110, 112 comprise different radial positions or radial mechanical structures, the at least one electric sensor 51 may be implemented as an electromechanical switch 56, 57 typically biased in radial direction and configured to mechanically engage with at least one of the radial protrusions or radial indentations on the tubular-shaped surface 102 of the first element 100 as for instance illustrated in FIG. 38.

The pattern 104 is not limited to only a first pattern portion 110 and a second pattern portion 112. There may be provided also third, fourth and numerous further pattern portions that distinguish from each other, thus allowing to implement not only a 2-bit pattern but supporting a 3-bit, 4-bit, 5-bit, 6-bit or even n-bit pattern, with n being an integer number larger than 0.

The type of pattern, hence the type of first and second pattern portions 110, 112 provided in the first pattern section 120 and provided in the second pattern section 122 may be substantially equal. However, the pattern and the pattern portions 110, 112 of the first pattern section 120, in particular their geometry, shape and orientation may distinguish from respective pattern portions 110, 112 provided in the second pattern section 122.

With other examples the type of first and second pattern portions 110, 112 in the first pattern section and the second pattern section may distinguish. For instance the first pattern section 120 may be provided with first and second pattern portions 110, 112 that distinguish with regard to their electrical conductivity. First and second pattern portions 110, 112 provided in the second pattern section 122 may for instance distinguish with regard to their radial position. Here, the first and the second pattern portions 110, 112 in the second pattern section 122 may comprise at least one of radial indentations or protrusions.

Figure 10:
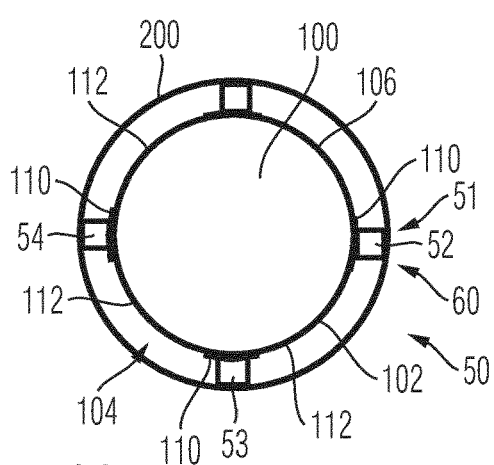
FIG. 10 is a cross-section through the first and the second elements in a first rotational state or configuration of the first element.

In FIG. 10 a cross-section through the first and the second element 100, 200 is illustrated in a first configuration. Here, the first element 100 comprises a pattern 104 on its outer circumference. The pattern 104 comprises four first pattern portions 110, e.g. implemented as electrically conductive stripes and further comprises four second pattern portions 112 located tangentially between the first pattern portions 110. The second pattern portions 112 may be electrically insulating. The electric sensor 51 comprises numerous electric contact taps 52, 53, 54 that are arranged on an inside surface of the second element 200.

Figure 11:
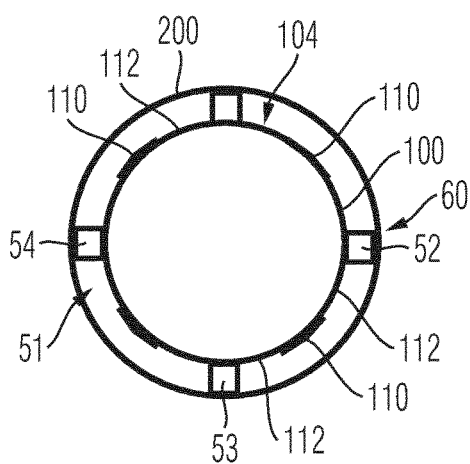
FIG. 11 shows the arrangement of FIG. 10, wherein the first element is in a different rotational state compared to the configuration of FIG. 10.

As illustrated in FIG. 10 a circumferential or tangential distance between neighboring contact taps 52, 53, 54 substantially equals a circumferential or tangential distance between neighboring first pattern portions 110. In FIG. 10, at least two of the contact taps 52, 53 are in electric contact with at least two of the first pattern portions 110. Moreover, every and all contact taps 52, 53, 54 may be in electric contact with a respective first pattern portion 110. In the example of FIGS. 10 and 11 the first pattern portions 110 and the arrangement of the electric sensor 51 with numerous contact taps 52, 53, 54 comprise the same periodicity as seen in circumferential or tangential direction of the tubular-shaped surface 102. So in the configuration of FIG. 10 all or at least some of the contact taps 52, 53, 54 will be electrically connected to at least one of the electrically conductive first pattern portions 110.

As the first element 100 is subject to a rotation relative to the second element 200, e.g. during one of the first movement and the second movement the first pattern portions 110 are subject to a circumferential or tangential displacement relative to the electric contact taps 52, 53, 54. In effect, the electrical contact taps 52, 53, 54 and hence the at least one electric sensor 51 will be out of contact with regard to the conductive first pattern portions 110. This results in a change of the electric signal obtainable from the at least one electric sensor 51 or obtainable from at least one of the contact taps 52, 53, 54.

In the example of FIGS. 10 and 11 the detector arrangement 50 is implemented as an incremental rotation detector operable to generate at least one electric signal as the first pattern portions 110 gets in contact with the electrical contact taps 52, 53, 54 or when the first pattern portions 110 gets out of contact with the contact taps 52, 53, 54. Here, numerous first pattern portions 110 simultaneously engage or disengage the numerous contact taps 52, 53, 54 thus providing a redundancy of the detector arrangement 50. For a detection and/or measuring of a rotation of the first element 100 relative to the second element 200 it is generally sufficient when at least one of the first pattern portions 110 engages or disengages at least one of the electrical contact taps 52, 53, 54.

Of course, the number and the arrangement of the first and second pattern portions 110, 112 as well as the number and arrangement of numerous contact taps 52, 53, 54 may vary. For increasing a detection range or measuring range of the detector arrangement 50 it may be beneficial that the pattern 104 comprising first and second pattern portions 110, 112 is irregular as seen in circumferential or tangential direction. In effect, the circumferential or tangential size of first and second pattern portions may vary.

There can be provided numerous first pattern portions 110 that have a tangential extension or size that is different to the tangential direction or size of other first pattern portions 110. The same may be valid for the second pattern portions 112. In addition, a circumferential or tangential distance between neighboring first pattern portions and/or neighboring second pattern portions may differ and may be not identical along the circumference of the tubular-shaped surface 102. In this way a higher resolution of angular detection may be implemented with a minimum of mutually interacting components on the first element 100 and the second element 200.

Figure 12:
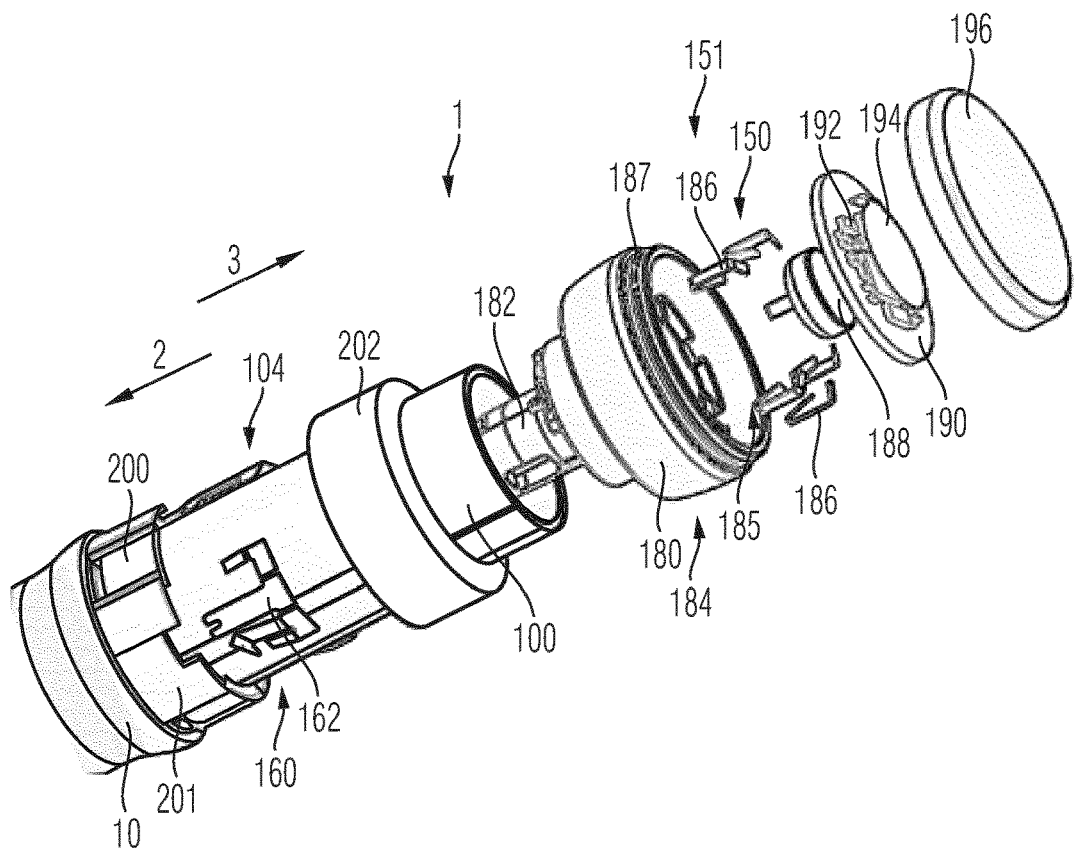
FIG. 12 is an exploded view of one example of an implementation of the injection device.
Figure 13:
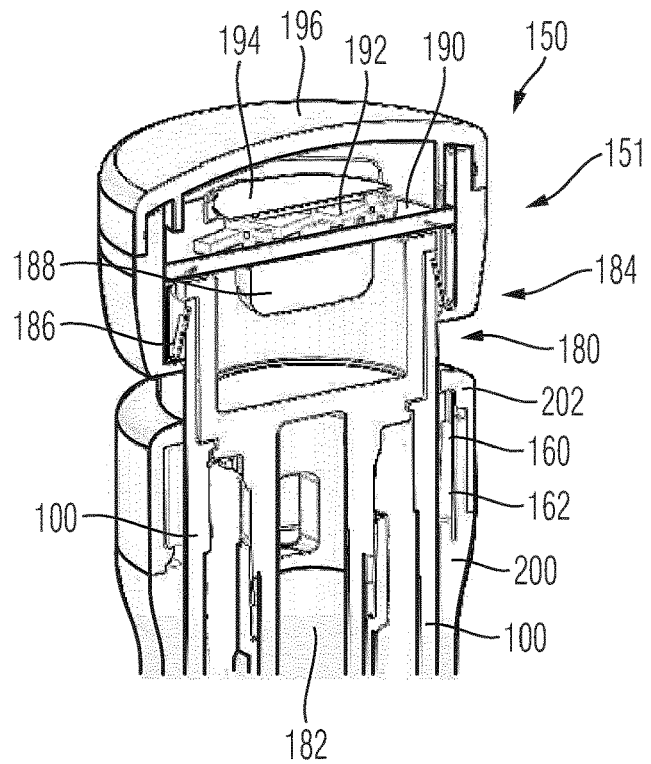
FIG. 13 is a perspective longitudinal cross-section through the device of FIG. 12.
Figure 14:
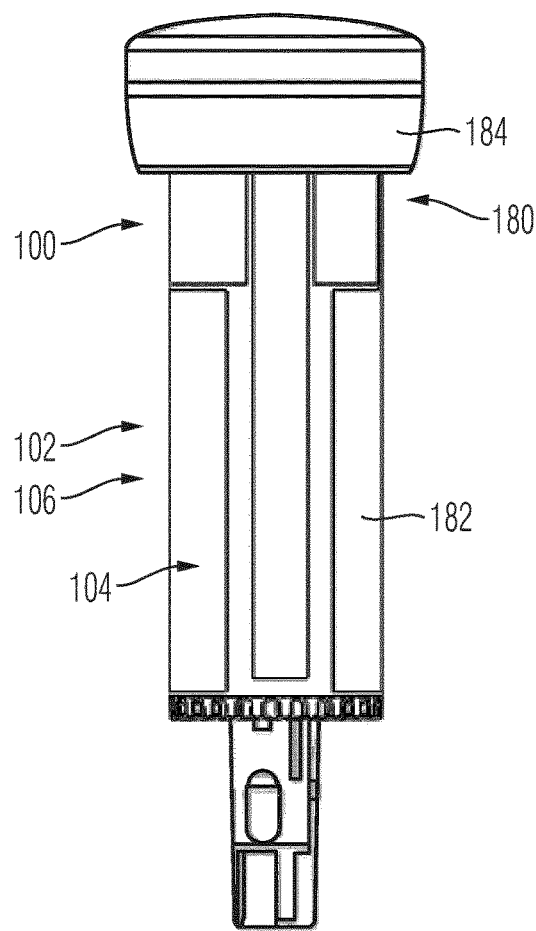
FIG. 14 is a side view of a further example of the first element.
Figure 15:
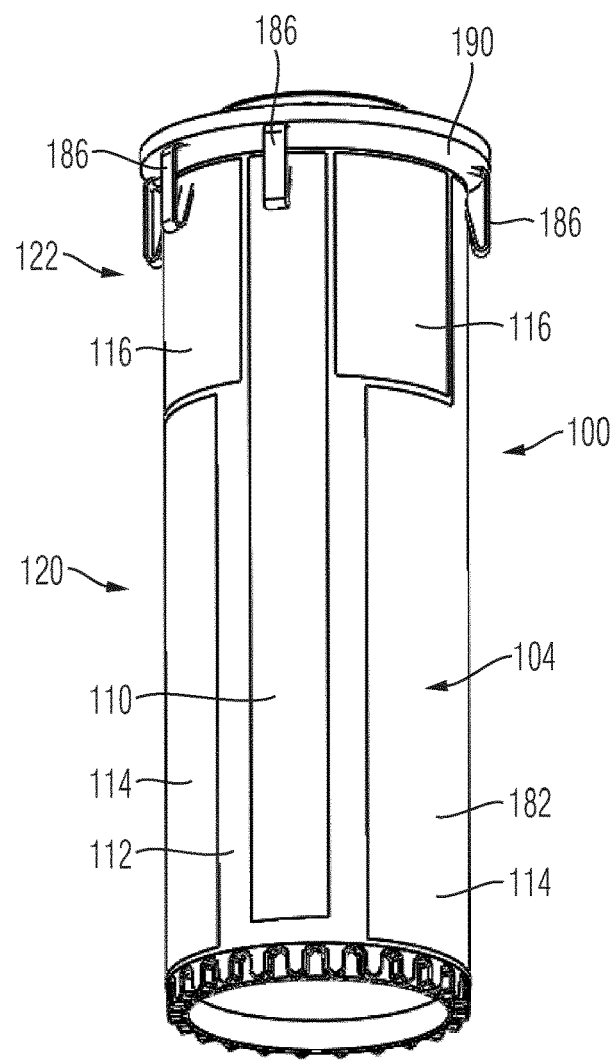
FIG. 15 is a perspective illustration of the first element according to FIG. 14.
Figure 16:
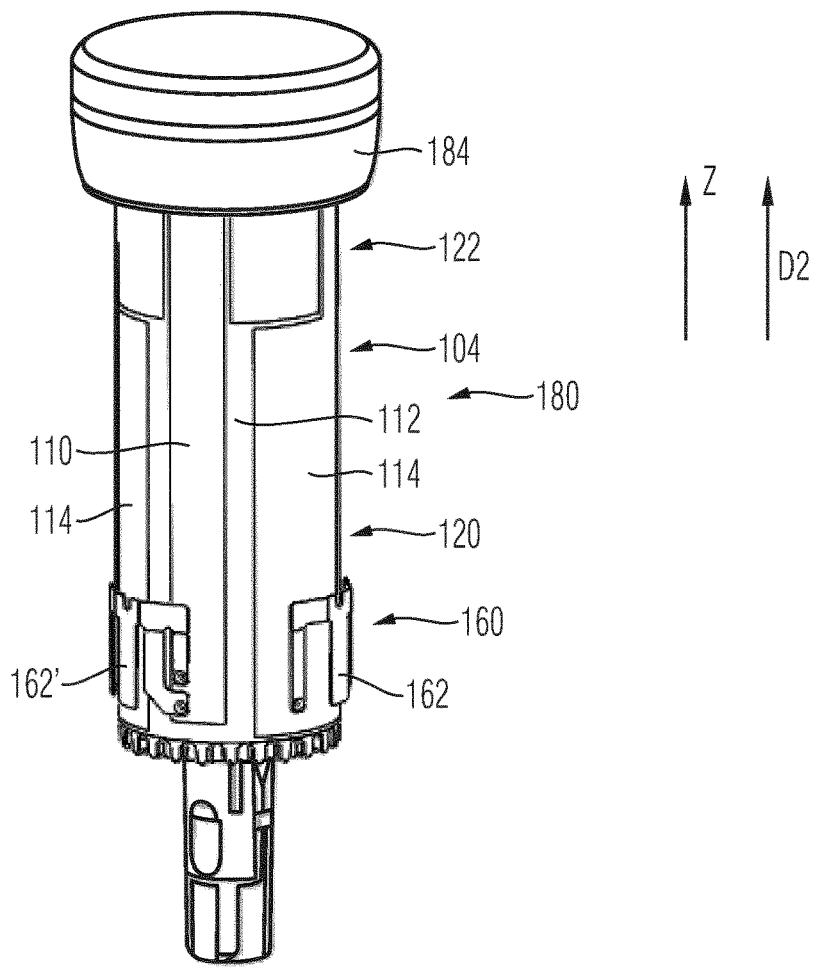
FIG. 16 is illustrative of the first element of FIGS. 14 and 15 together with the reference element.
Figure 17:
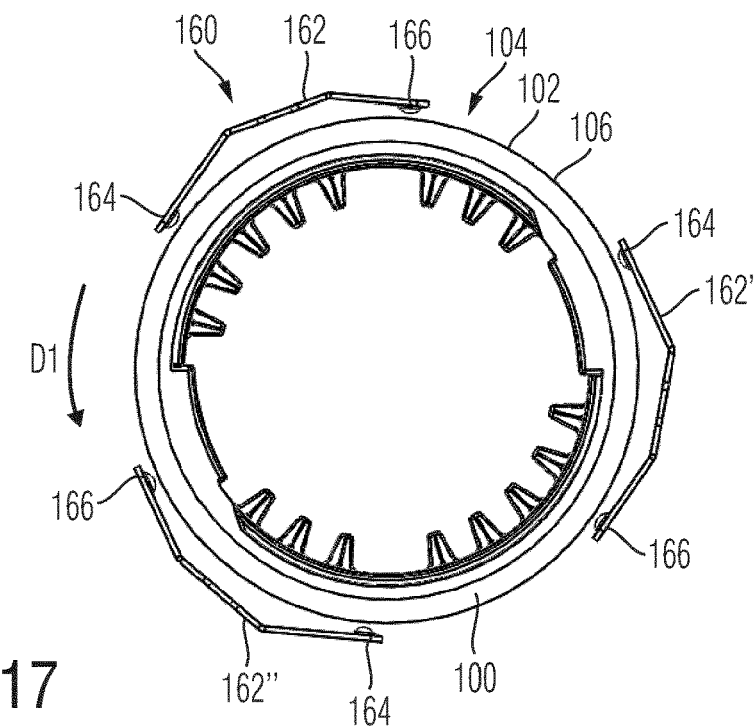
FIG. 17 shows a cross-section through the assembly of FIG. 16 with three separate reference elements.

In FIGS. 12 and 13 a possible implementation of the detector arrangement 150 in a pen-type injection device 1 is shown in more detail. The injection device 1 comprises a tubular-shaped housing 10 with a tubular body 201. The body 201 is open towards the proximal direction 3. The housing 10 represents the second element 200 in accordance to the present disclosure. The first element 100 is of tubular shape. It comprises a tubular-shaped sleeve that is telescopically arranged inside the second element 200. The first element 100 may be a dosing or dose dial sleeve. It may be rigidly and unmovably connected to a dial 180. The housing 10 and hence the second element 200 is closed in proximal direction 3 by a retaining cap 202 attached to the proximal end of the sidewall of the second element 200.

There are provided numerous reference elements 160 that are fixedly arranged at an inside surface of the sidewall of the second element 200. By way of example the reference elements 160 are implemented as electrical bridging contacts 162. They may be kept in position at or on the inside surface of the second element 200 through the retaining cap 202. The retaining cap comprises a central through opening, through which the first element 100 is allowed to protrude in longitudinal direction. The first element 100, in particular its tubular sleeve is rotationally fixed to the dial 180. It is also axially engaged with the dial 180. It may be rigidly connected to the dial 180 such that any rotational and/or longitudinal sliding movement of the dial 180 equally transfers to the first element 100.

The dial 180 comprises an annular-shaped and radially widened head section 184 providing a hollow receptacle 185 for the detector arrangement 150. The dial 180 further comprises a longitudinally extending dial sleeve 182 rigidly connected to or integrally formed with the head section 184. The head section 184 forms a proximal end of the dial 180. The outer circumference of the annular-shaped head section 184 comprises a diameter that may substantially match with the outer diameter of the second element 200. The head section 184 is open towards the proximal direction 3. It comprises an annular or tubular-shaped sidewall 187 to which a closure 196 in form of a closure cap or lid can be attached so as to close the receptacle 185.

Figure 18:
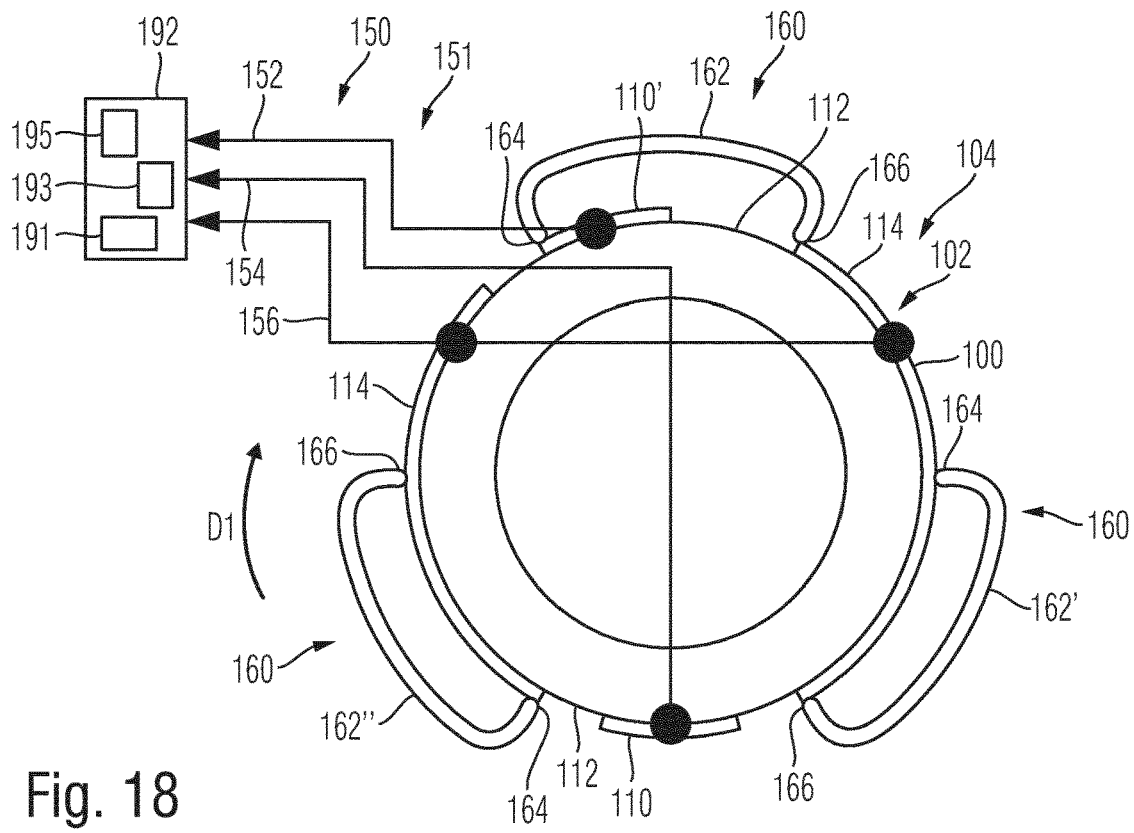
FIG. 18 is a schematic cross-section of FIG. 17 illustrating an electrical circuitry of the pattern provided on the first element relative to the reference elements.

Inside the receptacle 185 the electronic components of the detector arrangement 150 are be arranged. The detector arrangement 150 comprises a printed circuit board 190 on which an integrated circuit 192 is arranged. Typically and as schematically illustrated in FIG. 18 the integrated circuit 192 comprises at least a processor 191 and a storage 193 for at least temporally storing data retrieved or acquired by the detector arrangement 150. Optionally, the integrated circuit 192 is further equipped with a communication unit 195 typically implemented as a wireless communication unit to establish wireless signal transmission with a further electronic device, such as a portable electronic device, e.g. a smartphone, a tablet computer or the like.

The detector arrangement 150 further comprises a battery 188. The battery can be assembled on one side of the printed circuit board 190 whereas the integrated circuit 192 is assembled on the opposite side of the printed circuit board 190. The integrated circuit 192 may be further covered by a cover 194. As illustrated in FIG. 12 there are provided numerous electrical contacts 186 that may be implemented as contact clamps, e.g. made of a sheet metal, such as stainless steel. One end of the electrical contact clamps 186 is connected to respective input terminals of the integrated circuit 192. The integrated circuit 192 may comprise numerous input terminals thus representing input channels for numerous electric sensors or for numerous contact taps of the electric sensor 151. An opposite end of the electric contact may extend through a sidewall or through a base of the dial 180 and may be in contact with the numerous pattern portions 110, 112, 114 of the pattern 104 of the first element 100. The electrical contacts 186 may be permanently connected to only one of the pattern portions 110, 112, 114. During dose setting and/or during dose dispensing the electrical contacts 186 may remain stationary with respect to the numerous pattern portions 110, 112, 114 as will be explained below.

Since any of the electrical contacts 186 is permanently connected with an input terminal of the integrated circuit 192 and is further permanently connected with one particular pattern portion of the pattern 110, 112, 114 of the first element 100 the present detector arrangement 150 does not have to be configured to read a code printed or provided on a tubular-shaped surface. Rather, the electrical state and/or the electrical properties of at least one of the numerous pattern portions 110, 112 is or are subject to a variation as the first element 100 is subject to at least one of the first movement and the second movement relative to the second element 200. Thus, the electrical contacts 186 form or constitute an input of the detector arrangement 150 and hence of the integrated circuit 192, e.g. implemented as a microcontroller operable to detect and to quantitatively measure or to determine a degree of rotation and/or longitudinal movement of the pattern 104 relative to the reference 160.

Figure 19:
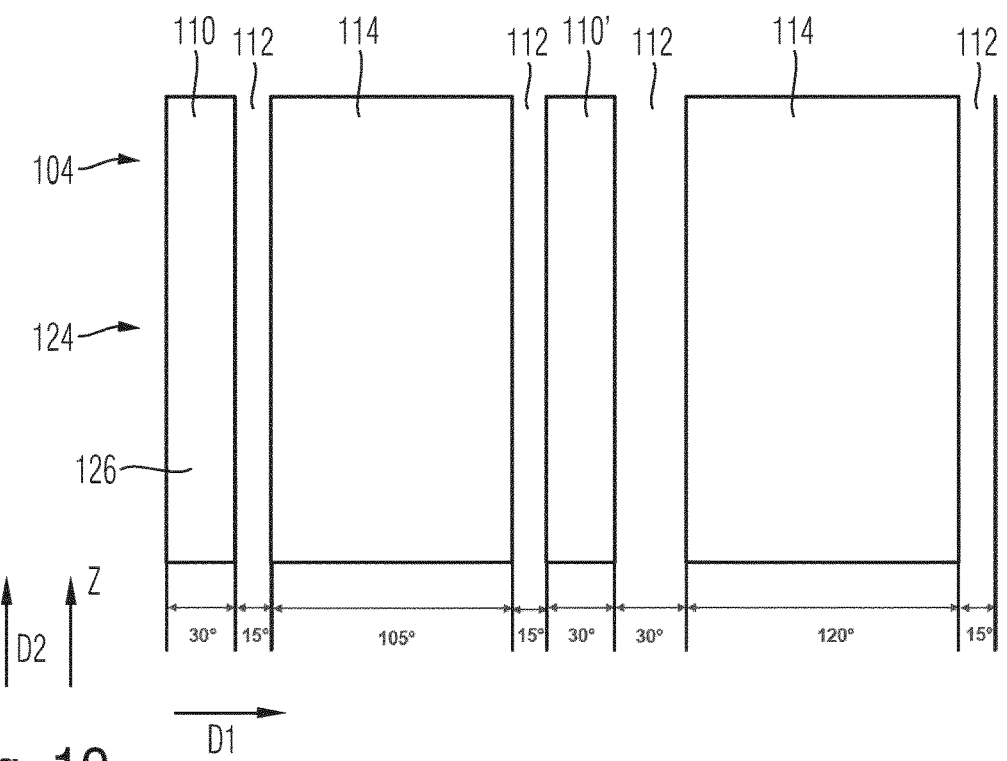
FIG. 19 shows the geometric structure of the pattern of the tubular-shaped surface of the first element according to FIGS. 14-18.

In FIGS. 18 and 19 one example of a 2-bit rotational encoder is illustrated. There are provided three separate reference elements 160 on or around a tubular-shaped inside surface of the second element 200. Each of the reference elements 160 comprises a bridging contact 162, 162', 162". For instance, the bridging contact 162 comprises a first contact tap 164 and a second contact tap 166 facing towards and preloaded in radial direction to get in mechanical contact with the pattern portions 110, 112, 114 provided on the pattern 104 of the tubular-shaped surface 102 of the first element 100.

The first and the second contact taps 164, 166 are separated from each other along a first separation direction D1. As illustrated in FIGS. 18 and 19 the first separation direction D1 extends along the circumference or tangential direction with regard to the tubular shape of the first element 100. The first contact tap 164 and the second contact tap 166 may be located apart by a predefined angle, e.g. by about 60°. The first and second pattern portions 110, 112 each comprise a longitudinal stripe. The first pattern portion 110 is a stripe with a width of 30°. The first pattern portion 110 is electrically conductive. The second pattern portion 112 being electrically insulating is located tangentially adjacent to the first pattern portion 110. The first pattern portion 110 comprises an angular or tangential width of about 15° to about 30°. There is further provided a third pattern portion 114 also implemented as an electrically conductive pattern portion. The third pattern portion 114 also comprises a longitudinal stripe and comprises a tangential or circumferential width of about 105° to about 120°.

As seen along the first separation direction D1 or as seen along the tangential direction the first pattern portion 110 is followed by a second pattern portion 112. The second pattern portion 112 is followed by a third pattern portion 114. The third pattern portion 114 is followed by a further second pattern portion 112. The further second pattern portion 112 is followed by a further first pattern portion 110'. The further first pattern portion 110' is followed by another second pattern portion 112 and the respective second pattern portion 112 is finally followed by a further third pattern portion 114. This third pattern portion 114 is again followed by a second pattern portion 112.

As illustrated in FIG. 19 the first pattern portions 110, 110' and the third pattern portions 114 are separated from each other by the second pattern portions 112. The first pattern portions 110, 110' are enclosed in both tangential directions by a second pattern portion 112. Also the third pattern portions 114 are enclosed in tangential direction by respective second pattern portions 112.

The first pattern portions 110, 110' are permanently electrically connected to input terminals of the detector arrangement 150. Here the pattern portion 110' is connected to a first input 152 of the detector arrangement 150. The further first pattern portion 110 is connected to a second input 154 of the detector arrangement 150. The third pattern portions 114 are electrically connected to a supply voltage 156. They may be mutually electrically interconnected. They may be provided with a predefined DC voltage level as the first element 100 is subject to a rotation relative to the second element 200.

As illustrated in FIG. 18 the numerous bridging contacts 162, 162', 162" are equispaced around the circumference of the first element 100.

As the first element 100 is subject to a rotation relative to the second element and as the pattern 104 is rotated relative to the reference 160 a rotational 2-bit gray code is detectable at the first and second input terminals of the detector arrangement.

In the rotational position as illustrated in FIG. 18 only the first pattern portion 110' is electrically connected to one of the third pattern portions 114 via the bridging contact 162. The other pattern portion 110 is disconnected from the pattern portions 114. Hence, there is provided a logical 1 at the first input terminal 152. As now the first element 100 and the pattern 104 are rotated clockwise relative to the reference 160 the contact tap 164 loses electrical contact from the first pattern portion 110'. This leads to a logical 0 at the first input terminal 152. In both configurations the second input terminal 154 and hence the other pattern portion 110 illustrated at the bottom in FIG. 18 is out of electric contact with regard to the further bridging contacts 162', 162".

Accordingly, the second input terminal 154 will remain at a logical 0 until the first element 100 is rotated further in clockwise direction. Then, the first contact tap 164 of the bridging contact 162" will get in electrical contact with the first pattern portion 110 thus generating a logical 1 at the second input terminal 154 while the first input terminal 152 remains at a logical 0. This is because the other, hence the second contact tap 166 of the bridging contact 162" is and remains in contact with the third pattern portion 114.

As the first element 100 is rotated further in clockwise direction the first contact tap 164 of the bridging contact 162 gets in contact with the third pattern portion 114 and the second contact tap 166 of the bridging contact 162 will get in contact with the first pattern portion 110'. This will generate a logical 1 also on the first input terminal 152. Thereafter and as the first element 100 is rotated further in clockwise direction relative to the second element 200 and hence relative to the reference element 160 the bridging contact 162" will lose contact with the pattern portion 110 by generating a logical 0 at the second input terminal. In this way, a 2-bit gray code 01, 00, 10, 11 can be generated as the first element 100 is rotated clockwise relative to the second element 200 by 60°. In this way, 24 discrete angular positions of the first element 100 relative to the second element 200 can be electronically detected. With the 2-bit gray code implementation not only the magnitude of a relative rotation but also the rotation direction can be precisely determined. The 2-bit gray code implementation requires that the detector arrangement 150 is counting a signal change at the first and the second input terminals 152, 154.

With the presently described implementation a step size of a relative rotation between the first element 100 and the second element 200 is about 15°.

The angular width of the first and hence electrically conductive pattern portions 110, 110' is twice the step size. The angular width of the second and electrically insulating pattern portions 112 is substantially equal to the step size or is substantially twice the step size. The angular position of the first pattern portion 110 and the further first pattern portion 110' is six times the step size. Hence, the angular offset between the first pattern portion 110 and the further first pattern portion 110' in one direction is 165°. The angular distance between the first pattern portion 110 and the further first pattern portion 110' is 135° in one direction and 165° in the other direction.

Figure 20:
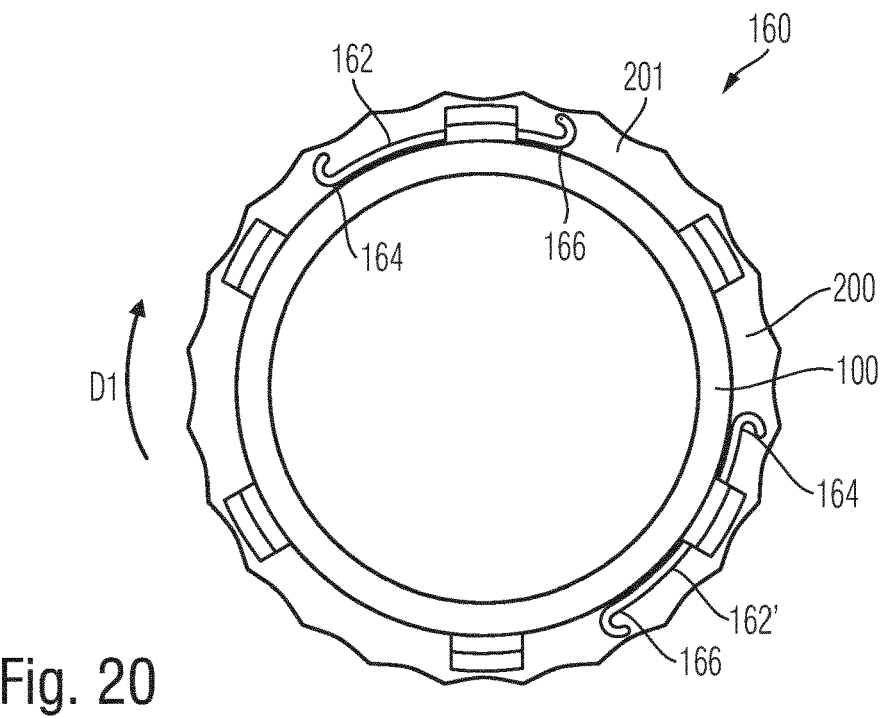
FIG. 20 shows another example of a detector arrangement comprising only two reference elements in connection with another example of a pattern on the tubular-shaped surface of the first element.
Figure 21:
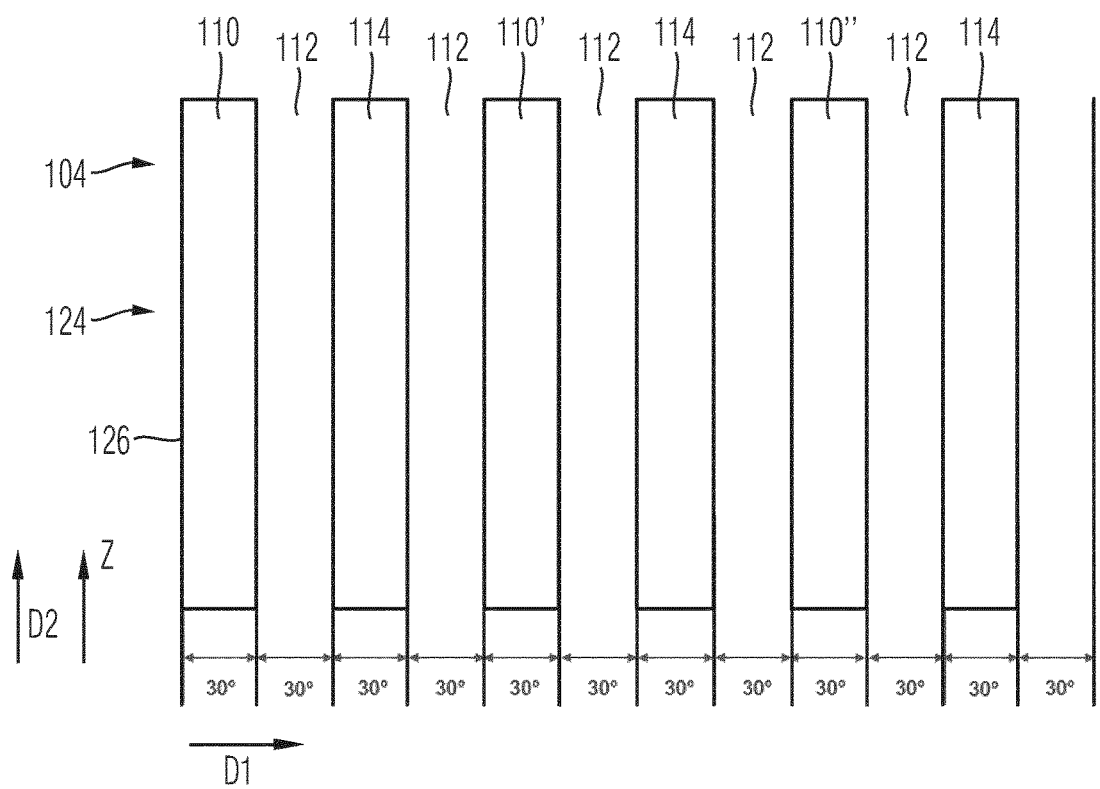
FIG. 21 shows the geometric structure of the pattern pursuant to FIG. 20, FIG. 22 schematically illustrates first, second and third electric contact taps of the reference element in a first longitudinal position of the first element relative to the reference element.

Another example of a 3-bit gray code implementation is shown in FIGS. 20 and 21. There, the pattern 104 comprises a stripe pattern 124 with numerous longitudinal stripes 126 comprising six equispaced conductive pattern portions 110, 114, 110', 114, 110", 114 and respective six insulating pattern portions 112 located therebetween. As illustrated in FIG. 21 and along the first separation direction D1 a first pattern portion 110 is followed by a second pattern portion 112. The second pattern portion 112 is followed by a third pattern portion 114. The third pattern portion is again followed by a further second pattern portion 112. This further pattern portion is again followed by a first pattern portion 110' and so on. Each pattern portion 110, 112, 114 comprises a substantial identical extension along the first separation direction D1. Here, each pattern portion 110, 112, 114 comprises an extension of about 30°.

The reference element 160 comprises two bridging contacts 162 as described above in connection with FIG. 18. The bridging contacts 162 each comprise a first contact tap 164 and a second contact tap 166. The first and the second contact taps 164, 166 are separated by an angular distance of about 50°. There is an angular offset between the first bridging contact 162 and the second bridging contact 162' of about 135°. Hence, the shortest angular distance between the second contact tap 166 of the first bridging contact 162 and the first contact tap 164 of the second bridging contact 162' is about 85°. Hence, the two bridging contacts 162, 162' are spaced apart from each other by 2.25 times the width of the stripes 126.

There are provided three pattern portions 114 that are permanently connected to a voltage supply. The three first pattern portions 110, 110', 110" are permanently connected to a first input terminal, to a second input terminal and to a third input terminal of the detector arrangement 150, respectively. In particular, the first pattern portion 110 is permanently electrically connected to a first input terminal. The further first pattern portion 110' is permanently electrically connected to a second input terminal and the further first pattern portion 110" is permanently electrically connected to a third input terminal.

With the configuration of the stripe pattern 124 and the reference element 160 as illustrated in FIGS. 20 and 21 the following 3-bit cyclical gray code can be implemented, wherein the individual doses comprise an angular offset of 15°.

| Doses dialled (U) | 1st input terminal | 2nd input terminal | 3rd input terminal |
|---|---|---|---|
| 0 | 0 | 0 | 0 |
| 1 | 0 | 1 | 0 |
| 2 | 1 | 1 | 0 |
| 3 | 1 | 0 | 0 |
| 4 | 0 | 0 | 0 |
| 5 | 0 | 1 | 0 |
| 6 | 1 | 1 | 0 |
| 7 | 1 | 0 | 0 |
| 8 | 0 | 0 | 0 |
| 9 | 0 | 0 | 1 |
| 10 | 0 | 1 | 1 |
| 11 | 0 | 1 | 0 |
| 12 | 0 | 0 | 0 |
| 13 | 0 | 0 | 1 |
| 14 | 0 | 1 | 1 |
| 15 | 0 | 1 | 0 |
| 16 | 0 | 0 | 0 |
| 17 | 1 | 0 | 0 |
| 18 | 1 | 0 | 1 |
| 19 | 0 | 0 | 1 |
| 20 | 0 | 0 | 0 |
| 21 | 1 | 0 | 0 |
| 22 | 1 | 0 | 1 |
| 23 | 0 | 0 | 1 |
| 24 | 0 | 0 | 0 |

The above illustrated cyclical gray code allows determination of a number of units dialed and to determine the direction of the rotation of the first element 100 relative to the second element 200. In addition, a degree of error checking is also possible as certain states cannot be reached.

The first element 100 only rotates relative to the second element 200 during one of the first movement and the second movement. For instance, the first element 100 only rotates relative to the second element 200 during and for setting of a dose. During or for dispensing or expelling of the dose of the medicament there is may be no relative rotation between the first element 100 and the second element 200. During such a non-rotating longitudinal sliding movement the longitudinal stripe pattern 124 may not generate an electrical signal.

In order to detect completion of a dose dispensing procedure the pattern 104 can be divided into a first pattern section 120 and a second pattern section 122 that are separated from each other along the longitudinal direction of the first element 100. In FIGS. 22 and 23 such a longitudinal separation, typically extending along a second separation direction D2 is schematically illustrated. Here, the first pattern portion 120 may comprise a stripe pattern 124 as illustrated and described above in connection with FIGS. 18-21. The stripe pattern 125 comprises numerous pattern portions 110, 112, 114 as described above. The reference element 160 may comprise a bridging contact 162 featuring at least a first electrical contact tap 164 and a second contact tap 166.

As described above the third pattern portion 114 may be permanently connected to a voltage supply 156. In the configuration as shown in FIG. 22 the first pattern portion 110, i.e. a conductive pattern portion is electrically connected to the third pattern portion 114 via the bridging contact 162. Here, the bridging contact 162 comprises a third contact tap 168 that is separated from at least one of the first contact tap 164 and the second contact tap 166 along the second separation direction D2. The second separation direction D2 extends non-parallel to the first separation direction D1. The second separation direction D2 extends at a predetermined angle with regard to the first separation direction D1. Typically and during the non-rotational longitudinal sliding movement between the first element 100 and the second element 200 the pattern 104 is subject to a sliding movement relative to the reference element 160 along the second separation direction. In the configuration as illustrated in FIG. 22 the third contact tap 168 is located on or in the first pattern section 120.

The first pattern section 120 is located longitudinally adjacent to the second pattern section 122. The first pattern section 120 and the second pattern section 122 are separated from each other by a separation 121, that can be implemented as a separation line. The separation 121 distinguishes with regard to the electrical conductivity and/or with regards to the electric state from at least one of the first pattern section 120 and the second pattern section 122.

The second pattern section 122 comprises a fourth pattern portion 116. The fourth pattern portion 116 is also a conductive pattern and is permanently connected to the detector arrangement 150 via at least one electrical contact 186 as described in connection with FIGS. 12 and 13. In the configuration as illustrated in FIG. 22 the second pattern portion 122 separated from the first pattern portion 120 along the second separation direction D2 is not in contact with the third contact tap 168. As the first element 100 and hence the pattern 104 is subject to a further sliding motion along the second separation direction D2, e.g. at the very end of a dose dispensing procedure, the third contact tap 168 traverses the separation 121 and gets in electrical contact with the fourth pattern portion 116.

At the same time the bridging contact 162 is and remains in electrical contact with the third pattern portion 114. In this way, an electrical conductive connection is formed between the third pattern portion 114 and the fourth pattern portion 116 as the first element 100 arrives at a predetermined longitudinal position with regard to the second element 200. For instance, the fourth pattern portion 116 can be provided with a respective supply voltage as the configuration as illustrated in FIG. 23 is reached, typically at the end of a dose dispensing procedure and when the first element returns into an initial state relative to the second element 200.

The traversing of the separation 121 and the establishing of an electrical contact between the fourth pattern portion 116 and the third pattern portion 114 can be detected by the detector arrangement 150. As the electrical contact is established the detector arrangement 150 detects that a zero dose configuration or the end of a dose dispensing procedure has been reached. In this way no further detector or switch will be necessary in order to detect a particularly longitudinal position of the first element 100 relative to the second element 200. The longitudinal displacement and the detection of at least one particular longitudinal position of the first element 100 relative to the second element 200 can be easily implemented into the detector arrangement 150 only by providing a further electrically conductive pattern portion 116 on the pattern 104 and by providing a further contact tap 168 on the bridging contact 162, wherein the further, hence the third contact tap 168 is separated from at least one of the further contact taps 164, 166 along the second separation direction D2 which may be somewhat parallel to the direction of the sliding motion between the first element 100 an the second element 200.

Figure 28:
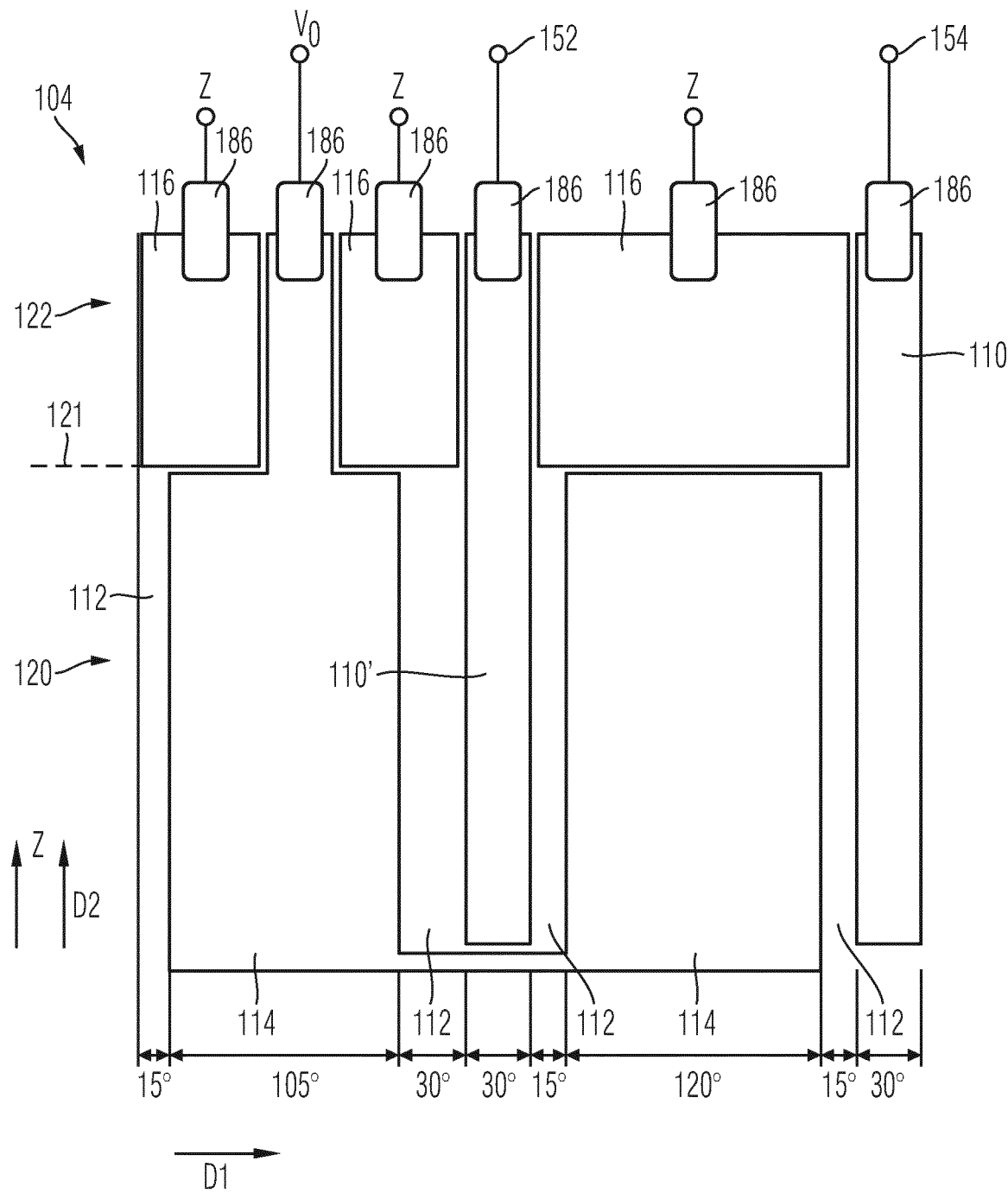
FIG. 28 is illustrative of another example of a pattern provided on the tubular surface of the first element.

In FIG. 28 a more detailed implementation of the pattern 104 including a first longitudinal pattern section 120 and a second longitudinal pattern section 122 is illustrated. In principle, the pattern 104 as illustrated in FIG. 28 is quite similar to the pattern 104 as illustrated in FIG. 19. There are provided two third pattern portions 114 that are permanently connected to a voltage supply Vo via an electrical contact 186. At a longitudinal end of the first pattern section 120 facing away from the second pattern section 122 the two third pattern portions 114 are mutually interconnected. At a longitudinal distance from this longitudinal end the two third pattern portions 114 are separated from each other by an angular distance of about 75°. In this angular section there is provided one first pattern portion 110' electrically insulated from the third pattern portions 114 by insulating pattern portions 112.

There is provided a small but distinct insulating longitudinal gap between the longitudinal end of the first pattern portion 110' and the interconnection between the two third pattern portions 114. The electrically conductive first pattern portion 110' extends in longitudinal direction almost along the entirety of the first pattern section 120 and intersects the second pattern section 122. It is electrically insulated from the further pattern portions 116 provided in the second pattern section 122. The longitudinal end of the first pattern portion 110' that is located in the second pattern section 122 is electrically connected to the first input terminal 152 of the detector arrangement 150. Another first pattern portion 110 comprises an elongated stripe 126 that is substantially identically shaped to the pattern portion 110'. This pattern portion 110 is connected via the electrical contact 186 to a second input terminal 154. Also this further first pattern portion 110 extends almost across the entirety of the first pattern section 120 and the second pattern section 122.

Only one of the third pattern portions 114 extends in longitudinal direction through the entirety of the second pattern section 122. There, the longitudinal end of the third pattern portion 114 located in or at the second pattern section 122 is connected to an electrical contact 186 and hence to a voltage supply.

The shape, the position and the angular separation of the numerous pattern portions 110, 110', 112 and 114 of the first pattern section 120 strongly resembles the pattern 104 as illustrated in FIG. 9 and provides a 2-bit quadrature encoding. In the second pattern section 122 the angular width of the third pattern portion 114 is reduced to 30°. Intermediate spaces in the second pattern section 122 between the first pattern portions 110, 110' and the third pattern portion 114 are substantially filled by fourth pattern portions 116. The fourth pattern portions 116 may be electrically interconnected. Each one of the fourth pattern portions 116 is connected to an electrical contact 186. Each electrical contact can be connected to a zero dose input terminal Z of the detector arrangement 150.

Figure 26:
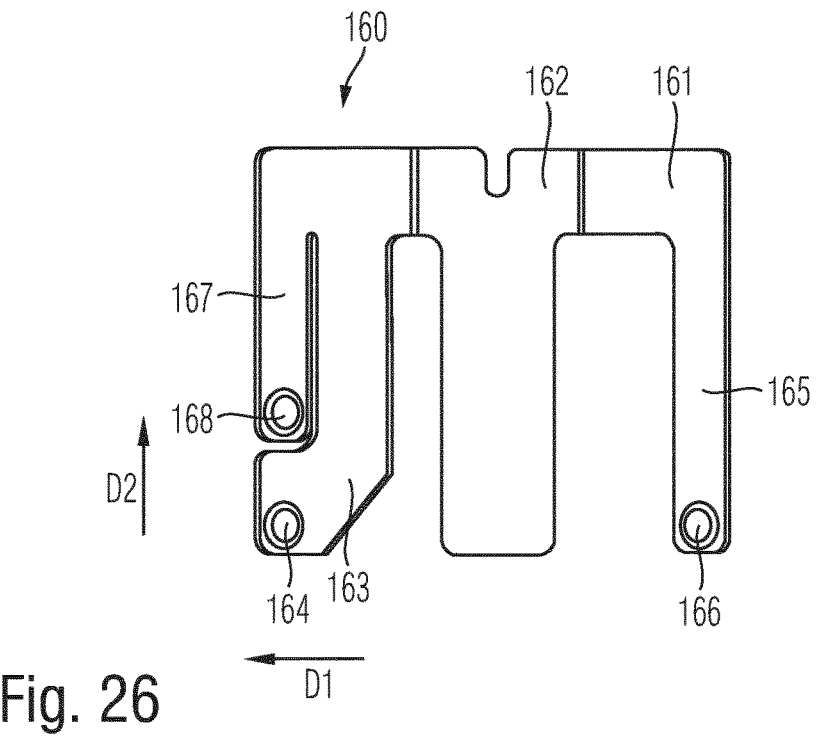
FIG. 26 is an isolated view of a reference element in accordance to FIGS. 16, 17, 24 and 25.
Figure 27:
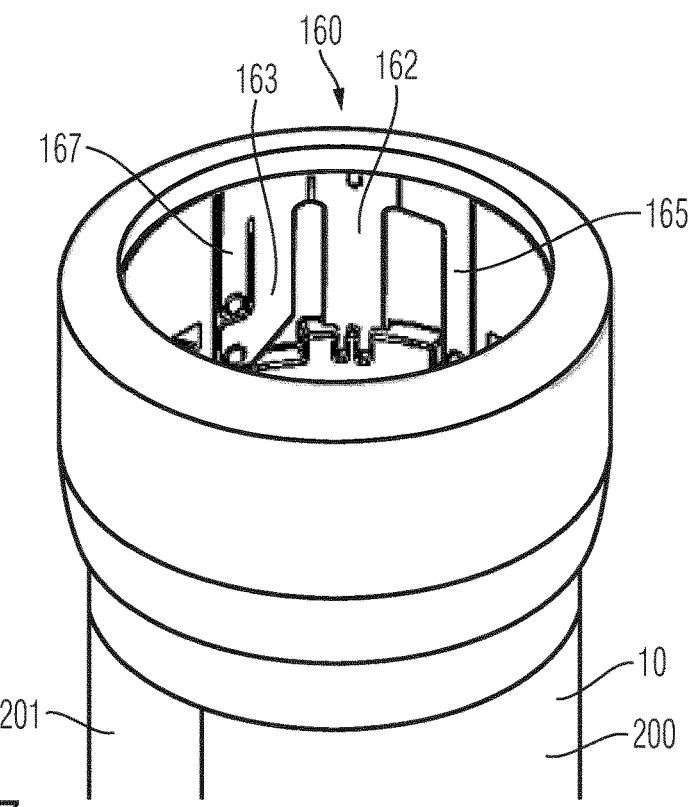
FIG. 27 is a perspective view of a proximal end of a housing of the injection device with the at least one reference element of FIG. 26.

The working principle of this 2-bit encoding with a supplemental zero dose position detection is illustrated in FIGS. 14-17 and with regard to FIGS. 24-26. The bridging contact 162 is fixedly connected to a tubular-shaped body 201 of the second element 200 as illustrated in FIG. 27. It is arranged at an inside tubular-shaped sidewall of the housing of the injection device 1. As illustrated in more detail in FIG. 26 the bridging contact 162 comprises three contact taps 164, 166, 168. The bridging contact 162 further comprises three flexible arms 163, 165, 167. The contact taps 164, 166, 168 are located at a longitudinal and hence at a free end of the respective flexible arms 163, 165, 167. All arms 163, 165, 167 as well as the respective contact taps 164, 166, 168 are electrically interconnected. The bridging contact 162 may comprise a piece of sheet metal.

As schematically illustrated and mentioned above the first contact tap 164 and the second contact tap 166 are separated from each other along a first separation direction D1. The first separation direction D1 may coincide with the tangential or circumferential direction of the tubular-shaped pattern 104. The first and the second contact taps 164, 166 may be arranged at the same longitudinal position. The third contact tap 168 is located at a longitudinal distance from at least one of the first and second contact taps 164, 166. It is typically separated in longitudinal direction along the second separation direction D2 from both of the first and the second contact taps 164, 166.

The contact taps 164, 166, 168 are integrally formed in the flexible arms 163, 165, 167. They may each comprise radially inwardly protruding embossed portions. The contact taps 164, 166, 168 may comprise a half dome-shaped structure and may thus protrude radially inwardly from the rather planar-shaped surface of the flexible arms 163, 165, 167. In this way, and due to the non-negligible radial protrusion of the contact taps 164, 166, 168 there may be provided a good and reliable mechanical and hence electrical contact between the contact taps 164, 166, 168 and the electrically conductive structures, hence with numerous pattern portions 110, 114, 116 of the pattern 104 of the first element 100. Typically, the flexible arms 163, 165, 167 and the radial protrusion of the respective contact taps 164, 166, 168 provide a kind of a radial preload as the first element 100 is arranged inside the hollow tubular-shaped second element 200.

A comparison of FIGS. 24 and 25 reveals the function of the third contact tap 168. In FIG. 24, the first element 100 is subject to a non-rotating distally directed sliding motion relative to the second element 200 and hence relative to the numerous bridging contacts 162, 162'. In the configuration of FIG. 24, the first element 100 is located close to a zero dose position but has not yet reached this zero dose position. Here, the first pattern portion 110 is in electrical contact with the third pattern portion 114 via the bridging contact 162. In this configuration the third contact tap 168 is located in the first pattern section 120. Hence, it is located distally from the separation 121.

Now, and as the first element 100 approaches and reaches the zero dose configuration relative to the second element 200 and hence relative to the reference element 160 as illustrated in FIG. 25 the third contact tap 168 has traversed the separation 121 and gets in electrical contact with the fourth pattern portion 116 while the first contact tap 164 remains in electrical contact with the third pattern portion 114. In this way, the supply voltage present on the third pattern portion 114 is provided also to the fourth pattern portion 116. As indicated in FIG. 28 the input terminal Z of the detector arrangement 150 is then tied to the supply voltage and switches from a logical 0 to a logical 1 as the zero dose configuration as illustrated in FIG. 26 has been reached. In this way, the zero dose position of the first element 100 relative to the second element 200 can be precisely detected at the end of a dose dispensing procedure.

In FIGS. 29-37 another example of a detector arrangement 50 is schematically illustrated. Also here, the first element 100 comprises a dial 180 or dial extension comprising a radially widened head section 184 with an annular outer gripping surface. The dial 180 further comprises a longitudinally extending dial sleeve 182 rigidly connected or integrally formed with the head section 184.

The first element 100 comprises a high degree of similarity compared to the examples as described above. The tubular-shaped first element 100 comprises a tubular-shaped surface 102, which is actually an outer surface 106. On the outer surface there is provided a pattern 104. The pattern 104 comprises a first pattern section 120 and a second pattern section 122. The first pattern section 120 extends almost over the entirety of the longitudinal elongation of the dial sleeve 182. The second pattern section 122 is located at or near a distal end of the first element 100 and hence at a distal end of the dial sleeve 182. The pattern 104 comprises numerous pattern portions 110, 112. The pattern portions 110 are electrically conductive. The pattern portions 112 are electrically insulating. There is further provided a fourth pattern portion 116 which is exclusively located in the second pattern section 122. The pattern portions 110, 112 comprise an elongated shape. They form a stripe pattern 124 comprising numerous elongated or rectangular-shaped stripes 126.

The detector arrangement 50 comprises at least one electric sensor 51 that is arranged on the second element 200, which is not particularly illustrated in the sequence of FIGS. 29-37. The at least one electric sensor 51 comprises or forms at least one reference element 60. The at least one electric sensor 51 is non-moveably attached and/or arranged at an inside facing surface of the second element 200.

Figure 29:
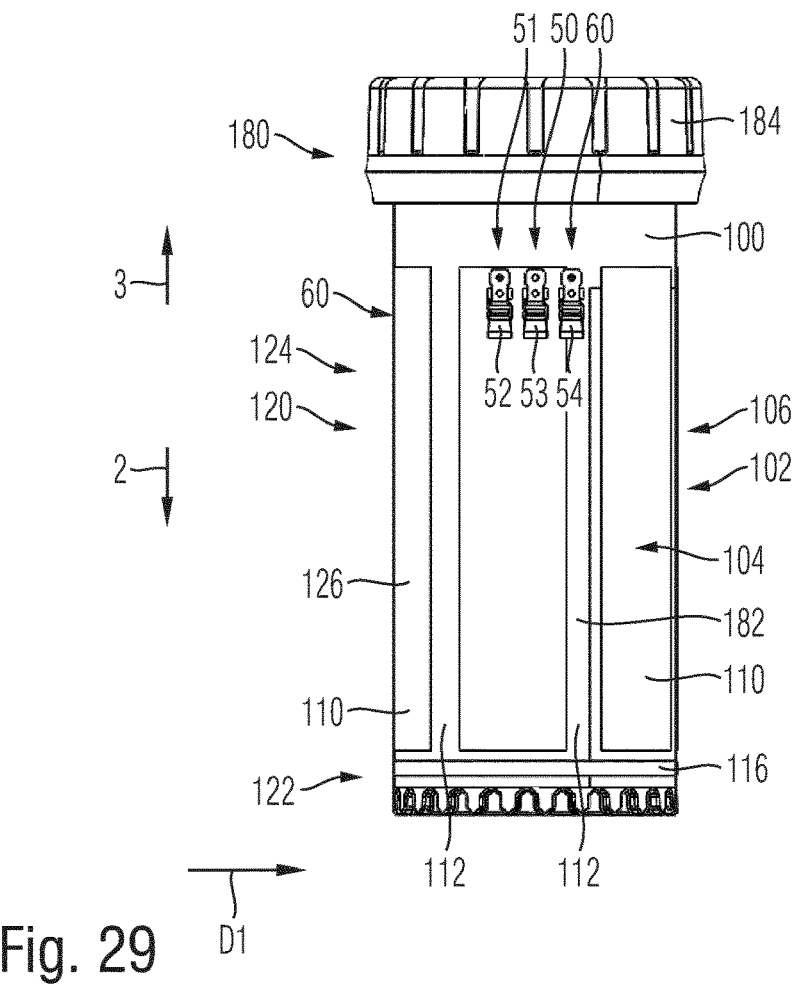
FIG. 29 is illustrative of another example of the detector arrangement, wherein the reference element comprises three electric contact taps arranged on the second element.

As illustrated in FIG. 29 the at least one electric sensor 51 comprises three electrical contact taps 52, 53, 54. The contact taps 52, 53, 54 are located at the same longitudinal position. They are separated along a first separation direction D1, hence along the tangential direction of the tubular shape of the surface 102. The numerous contact taps 52, 53, 54 are configured to get in electrical contact with the pattern portions 110, 112 alternately as the pattern 104 is subject to a rotation relative to the reference element 60, hence as the first element 100 is rotated relative to the second element 200. The distance and/or the separation between neighboring contact taps 52, 53, 54 along the first separation direction D1 is typically smaller than the width of the electrically conducting pattern portions 110 in the respective separation direction D1.

It is even conceivable, that the total separation of the two outer contact taps 52, 53 along the first separation direction D1 is smaller than the respective width of the first pattern portion 110.

Figure 30:
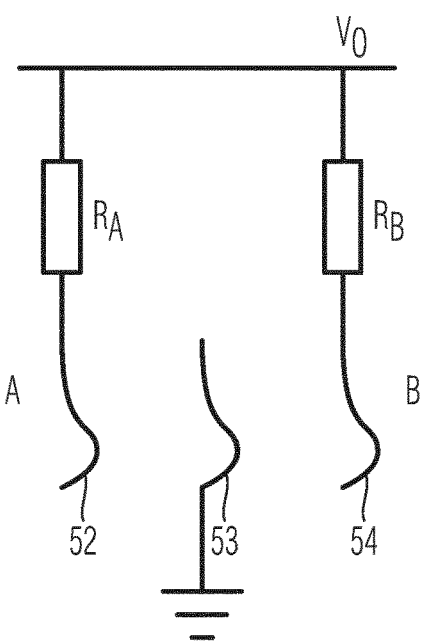
FIG. 30 is illustrative of the electric circuitry of the electric sensor of FIG. 29.

In FIG. 30, one example of an electric circuitry showing the three contact taps 52, 53, 54 is schematically illustrated. The two outer contact taps 52, 54 may be each permanently connected to a respective input terminal A, B of the sensor arrangement 50. These two contact taps 52, 54 may be connected to a voltage supply Vo via respective resistors $R_A$ and $R_B$. The further contact tap 53 may be connected to ground. The resistors may be regarded as pull-up resistors. In the sequence of FIGS. 31-34, numerous rotational states of the pattern 104 relative to the reference 60 are illustrated.

Figure 31:
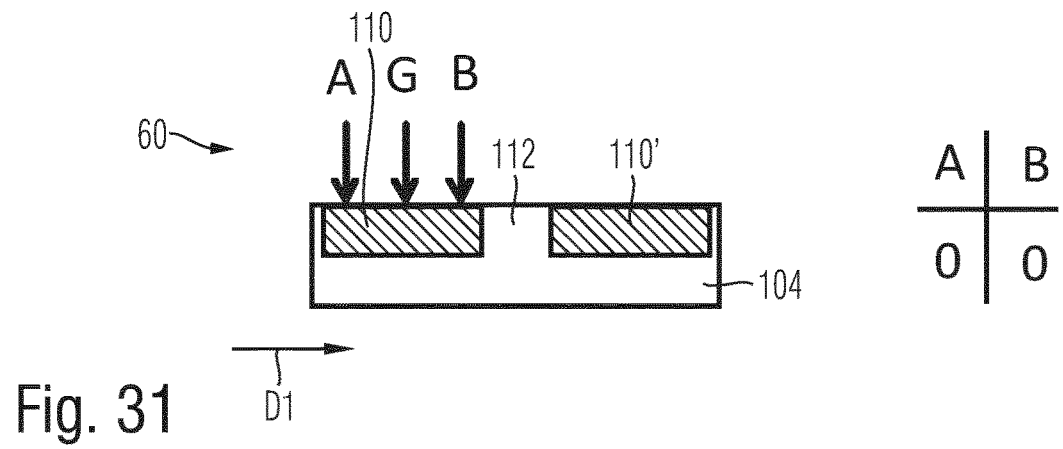
FIG. 31 is illustrative of a first rotational state of the first element relative to the reference.
Figure 32:
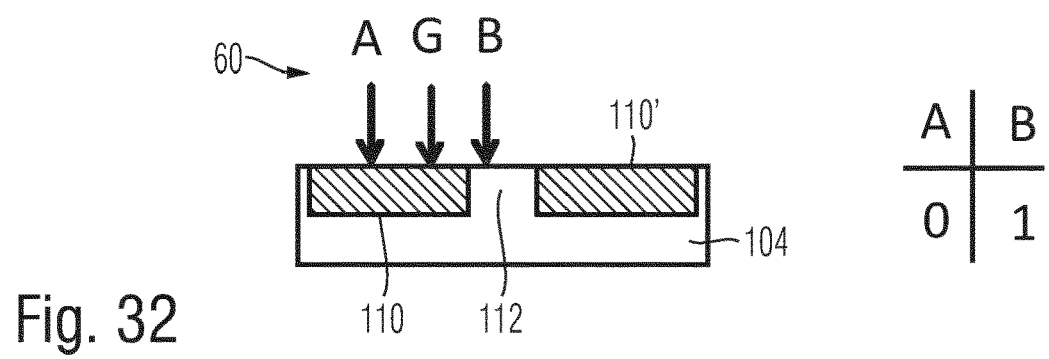
FIG. 32 is illustrative of a second rotational state of the first element relative to the reference.

Here, the position of the contact tap 52 is represented by A, the position of the contact tap 53 is representing by G and the position of the contact tap 54 is represented by B. In the configuration as illustrated in FIG. 31 all three contact taps are electrically connected to each other via the electrically conductive pattern portion 110. As the pattern 104 is subject to a rotation only one of the contact taps, namely contact tap 54 gets out of contact with regard to the electrically conducting pattern portion 110. As illustrated in FIG. 32 the contact tap 54 and hence the contact B is electrically connected to the insulating pattern portion 112. As a consequence the contact tap 54 is no longer connected to the contact tap 53 and is hence no longer connected to ground. As a result, the respective input terminal B of the detector arrangement 50 is switched to logical 1 while the other input terminal A connected to the contact tap 52 remains at a logical 0.

Figure 33:
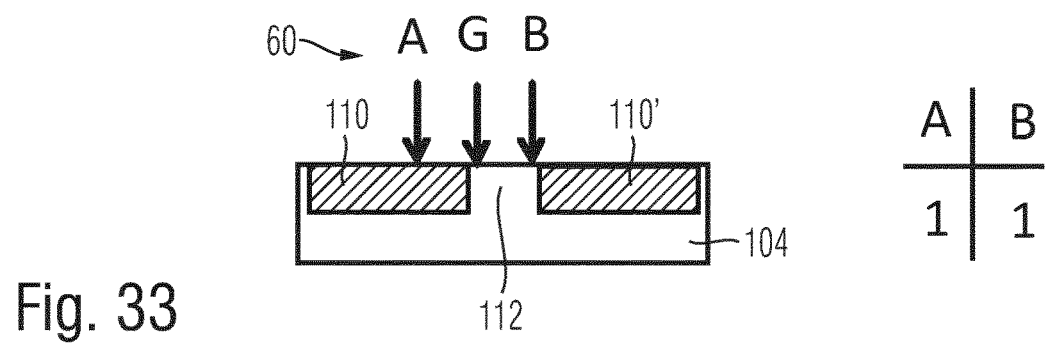
FIG. 33 is illustrative of a third rotational state of the first element relative to the reference.
Figure 34:
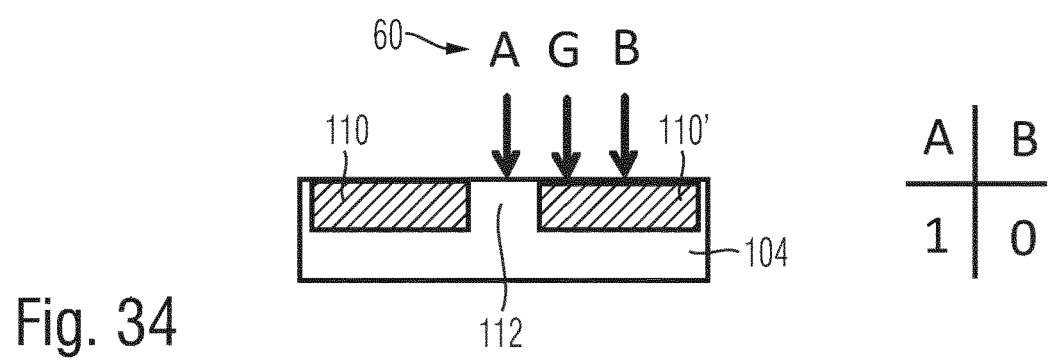
FIG. 34 is illustrative of a fourth rotational state of the first element relative to the reference.

As the pattern 104 is rotated further in the same direction, both, the contact tap 54 and the contact tap 53 are electrically insulated because they are both electrically connected to the insulating pattern portion 112. For this it is only important, that the contact tap 53 and hence the contact tap 53 connected to ground is electrically isolated from the other two contact taps. Accordingly, both input terminals A and B are at the logical 1 as illustrated in FIG. 33. As further illustrated in FIG. 34 and as the pattern 104 is rotated further both contact taps 53 and 54 are electrically connected via the further conductive pattern portion 110'. Accordingly, the input terminal B is switched to logical 0 while the input terminal A is electrically connected to the insulating pattern portion 112. Accordingly, a respective input voltage can be sensed at the input terminal of the detector arrangement 50.

The angular width or the tangential extension of the conductive pattern portions 110, 110' may be equal to or may be in a range of 45°. The respective extension or size of the insulating pattern portion 112 is substantially smaller than the extension or width of the first pattern portion 110, 110'. The extension or size of the first pattern portion 110, 110' may be three times as large as the respective width or size of the second pattern portion 110 along the first separation direction D1. The angular width of the second pattern portion 110 may be about 15°. In this way, a binary incremental quadrature encoder can be implemented. Since the stripe pattern 124 extends in longitudinal direction it is invariant with regard to a longitudinal displacement of the first element 100 relative to the second element 200.

Figure 35:
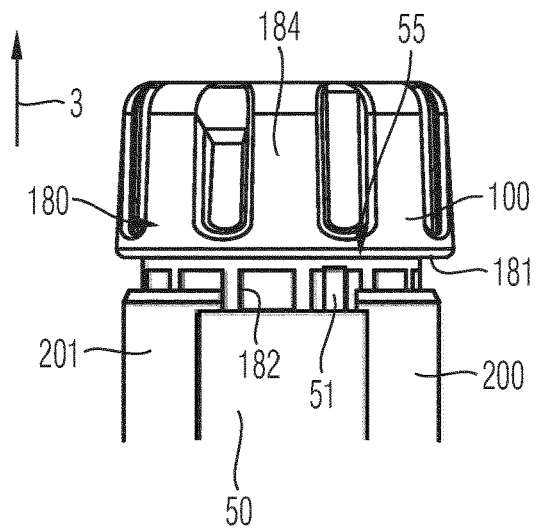
FIG. 35 shows a further example of a detector arrangement with another example of an electric sensor in an idle state.
Figure 36:
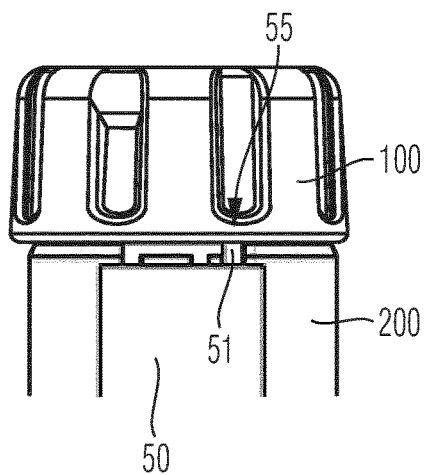
FIG. 36 is illustrative of the example of FIG. 35 with the electric sensor in an activated state.

In FIGS. 35 and 36 a further detector arrangement 50 is schematically illustrated. Here, the at least one electric sensor 51 comprises a switch 55 that is operable to mechanically engage with at least one of a radial recess, indentation or radial protrusion of the first element 100. Here and as illustrated in FIGS. 35 and 36 the first element 100 comprises a radially stepped portion 181 longitudinally adjacent to the dial sleeve 182. The stepped portion 181 forms a neck of the radially widened head section 184. The switch 55 axially protrudes from the body 201 of the second element 200. It extends in proximal direction 3 and it is configured to engage with the stepped portion 181 as the first element 100 and hence the dial 180 returns into a zero dose or end of dose configuration as illustrated in FIG. 36.

The radial position of the switch 55 overlaps with the radial position of the stepped portion 181. As the dial 180 and as the first element 100 returns into an initial state as illustrated in FIG. 36 the switch 55 is depressed in distal direction 2. When the electromechanical switch 55 is depressed at the end of a dose dispensing procedure a respective electrical signal is generated that is processable by the detector arrangement 50 which is located on or embedded in the second element 200.

Figure 37:
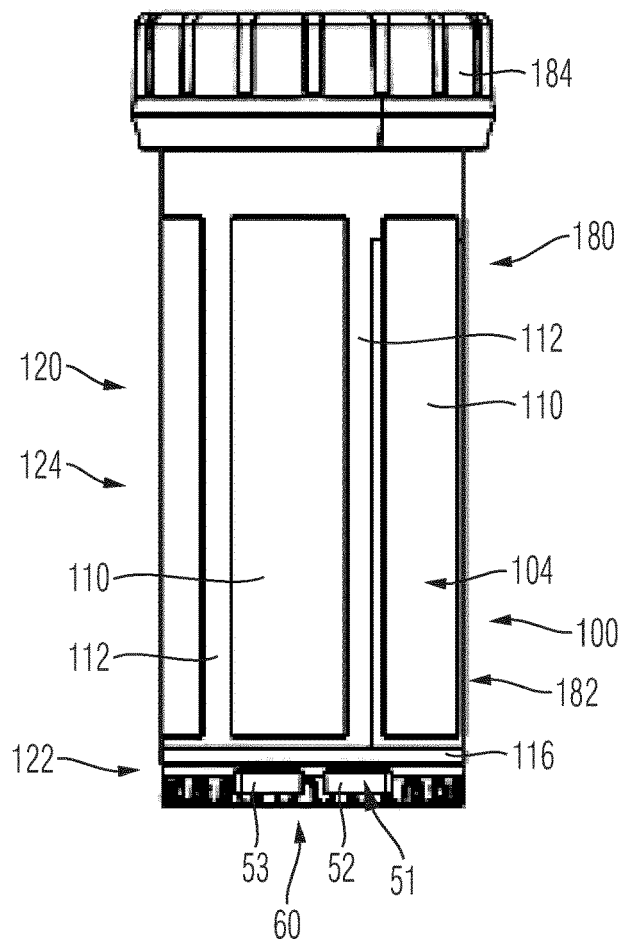
FIG. 37 is illustrative of another example of the detector arrangement.

As an alternative or in addition to the electromechanically implemented switch 55 there may be provided the second pattern section 122 at a longitudinal or distal end of the first element 100 as illustrated in FIG. 37. There, a fourth conductive pattern section 116 comprises an annular shape and is separated in longitudinal direction from the stripe pattern 124 which is exclusively located in the first pattern section 120.

The electric sensor 51 and hence the reference element 60 located and arranged on the second element 200 comprises two contact taps 52, 53 that are located at the same longitudinal position at a given separation in tangential direction. When the first element 100 approaches and reaches the end of dose or zero dose configuration as illustrated in FIG. 36 the contact taps 52, 53 overlap with the fourth conductive pattern portion 116. In effect, the two contact taps 52, 53 become electrically connected via the fourth pattern portion 116. As a consequence, an electric circuit including the two contact taps 52, 53 is closed by the pattern portion 116 and a respective electric signal is generated.

In FIG. 38 another example of a pattern 104 is illustrated. Here, the pattern 104 comprises a longitudinally extending stripe pattern with first and second pattern portions 110, 112 alternately arranged long the circumference or tangential direction of the tubular-shaped first element 100. Here, the first pattern portion 110 comprises a radially raised and hence radially outwardly protruding longitudinally extending rib or ridge 130. The second pattern portion 112 comprises a respective radial indentation or groove 132.

For the implementation of a binary encoding there are provided at least two electromechanically implemented switches 56, 57 that may be preloaded in radial direction. The switches 56, 57 are electrically connected to the at least one electric sensor 51. The switches 56, 57 are activated and/or deactivated as the raised ridges 130 and/or the grooves 132 rotate in tangential or circumferential direction.

There is further illustrated an axial or longitudinally acting switch 55 that can be depressed by the stepped portion 181 at a distal end of the head section 184 of the dial 180 as described above in connection with FIGS. 35 and 36.

Figure 39:
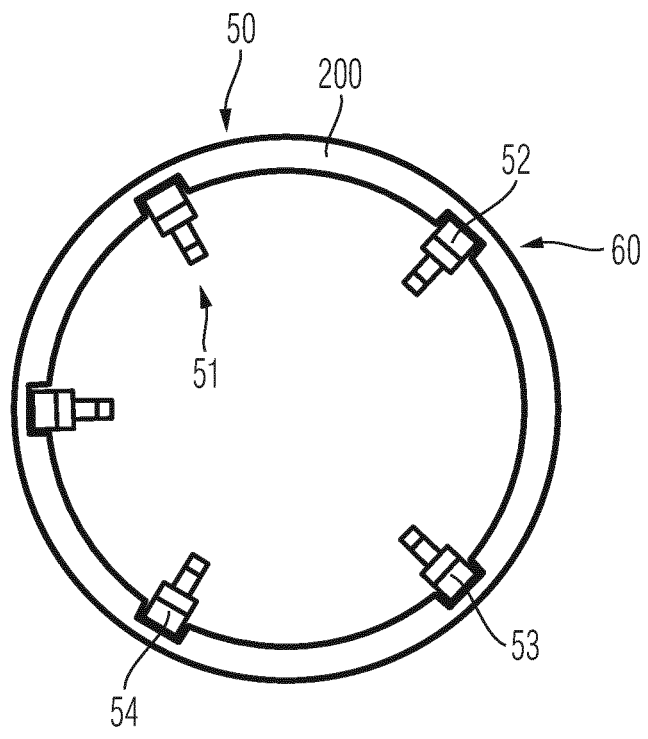
FIG. 39 shows another example of a reference element comprising five contact taps arranged along an inner circumference of a tubular-shaped second element.
Figure 40:
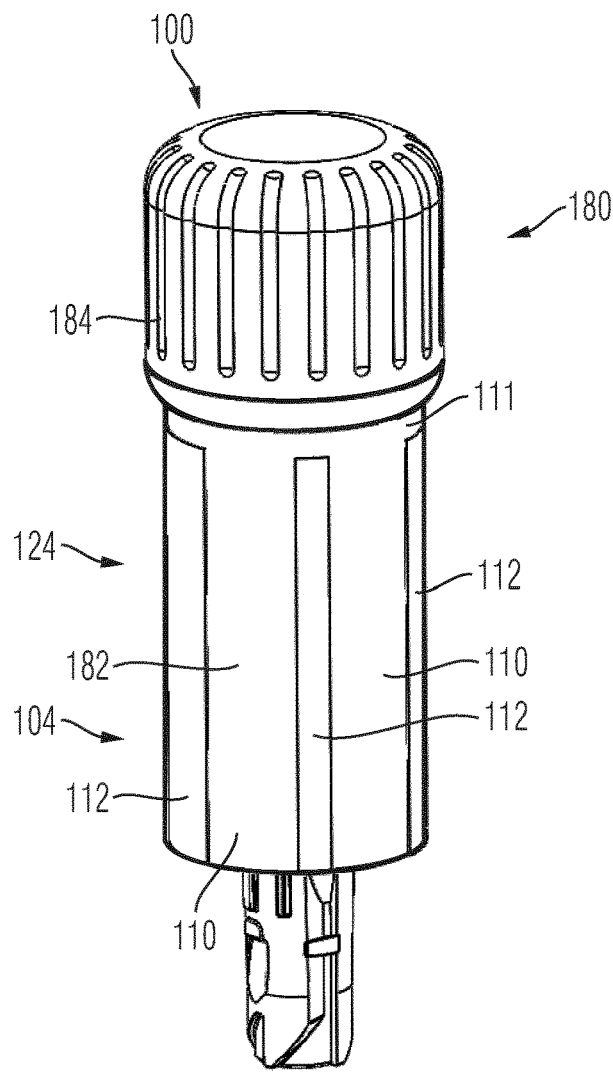
FIG. 40 is a perspective illustration of another example of the first element operable and configured to cooperate with the reference elements as illustrated in FIG. 39.
Figure 41:
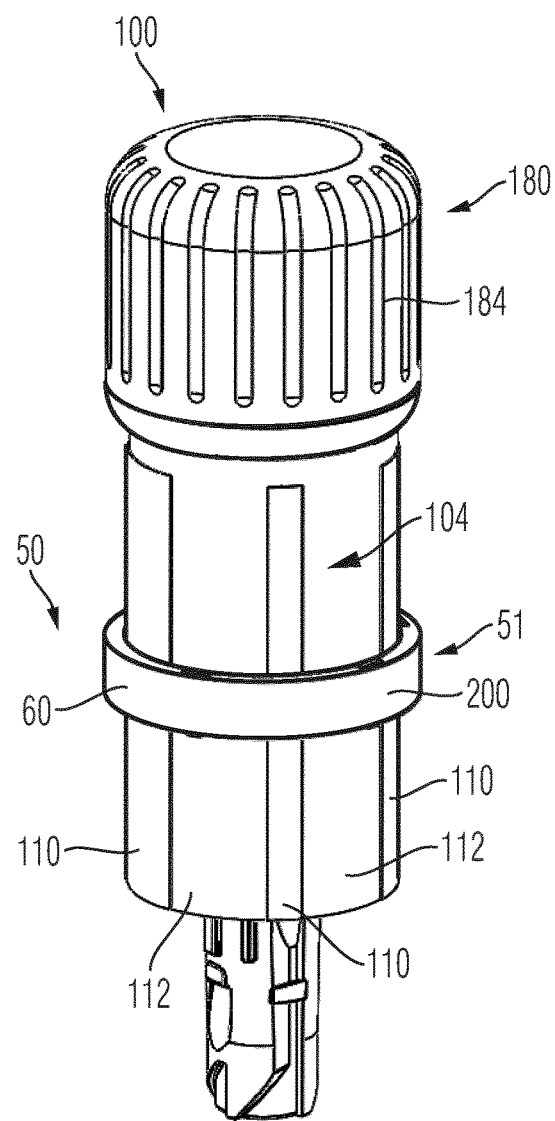
FIG. 41 shows the first element of FIG. 40 and the second element of FIG. 39 in an assembly configuration, FIG. 42 schematically illustrates the relative position of at least one cleaning pad in relation to at least one contact tap of the electric sensor in a side view of the first and the second elements.

In FIGS. 39-41 another example of an arrangement of five contact taps forming a reference element 60 is schematically illustrated. Here, a 5-bit absolute code can be provided, wherein each one of 24 rotational positions of the first element 100 relative to the second element 200 can be uniquely defined.

The pattern 104 as illustrated in FIGS. 40 and 41 is again a longitudinal stripe pattern 124 comprising numerous first pattern portions 110 that are electrically conducting and numerous pattern portions 112 that are electrically insulating. Contrary to the examples described above all electrically conducting pattern portions 110 are electrically connected via an annular-shaped pattern connecting portion 111 at a proximal or distal end of the pattern 104.

The numerous contact taps 52, 53, 54 and the two further contact taps as illustrated in FIG. 39 are positioned at 0°, 60°, 135°, 225° and 300° around the inner circumference of the second element 200. The pattern 104 can be characterized as a binary pattern, wherein a zero represents a 12° extension of an electrically insulating second pattern portion 112 and wherein a logical 1 represents a 15° tangential extension of an electrically conductive first pattern portion 110. Insofar, and for the given arrangement and distribution of five contact taps 52, 53, 54 as illustrated in FIG. 39 the code and hence the pattern 104 may comprise the following structure: 000001110000111011100011. Hence, an initial non-conductive pattern portion 112 extends over 75° in tangential direction followed by a 45° wide conductive pattern portion 110 followed by an insulating pattern portion 112 of 60°, followed by a 45° wide conductive pattern portion 110, followed by an insulating pattern portion 112 with a width of 15°, followed by a further conductive pattern portion 110 with a width of 45° followed by an insulating pattern portion 112 of 45° and finally followed by a conductive pattern portion with a width of 30°.

This code in connection with the arrangement of the five contact taps 52, 53, 54 of the electrical sensor 51 provides an absolute code with 24 unique positions. Presumed that the first element can be rotated a bit more than three times so that 80 possible rotational positions are provided during dialing, the respective rotational positions are inferred from the sequence in which the codes appear, giving a quasi absolute encoding solution for all dialed doses. Moreover and due to the unique code for each achievable rotational position of the first element 100 relative to the second element it is possible to apply an error checking algorithm when decoding the signal from the numerous contact taps 52, 53, 54. For example, it is not possible to move directly from a 2 unit position to 23 unit position, so if a '23 unit' code were observed when dialing between 2 units and 3 units it would be clear that it was an artifact of the transmission and would not be counted.

At a zero dose position, hence at the end of a dose dispensing procedure and when the first element 100 arrives at the distal most position with regard to the second element 200 at the end of a dose dispensing procedure all five contact taps 52, 53, 54 will contact the pattern connecting portion 111 at the proximal end of the first element 100. This will register as a unique code of 11111 which can be decoded by the electronics of the detector arrangement 50 to indicate a zero unit end of dose position. The example as illustrated in FIGS. 39-41 provides an increased level of robustness over incremental dose counting systems.

With all of the examples as described above use of electrical contact taps or switches allows the detector arrangement 50, 150 to have a low power consumption and removes a necessity to separately detect a mode shift when the device is dispensed as the device can remain powered on during its life cycle. This low power consumption, in conjunction with using, e.g. near field communication technology for the communication unit 195 allows a small battery and simpler microcontroller implementations thus making the example suitable for embedding within a disposable pen-type injection device.

The detector arrangement 50, 150 as described herein could be implemented and embedded in a disposable injection device 1. The detector arrangement 50, 150 may remain powered on for the duration of its life cycle. It may remain per default in a dormant state. The integrated circuit, hence the microcontroller of the detector arrangement 50, 150 could wake up on a first change of the electric sensor 51, 151 that is observed as the first element 100 is subject to a movement relative to the second element 200 for the first time.

The conductive pattern 104 and in particular the electrically conducting pattern portions 110, 114, 116 may be realized by making use of carbon-based conductive inks to create the pattern 104 on the tubular-shaped surface 102. Such carbon-based inks are available at low cost and are suitable for applications via rotary tampon printing when combined with appropriate thinning agents. The rotary tampon printing is a high volume manufacturing process. Moreover and in order to reduce the electrical resistance of the conductive ink it is possible to alloy carbon-based inks with silver-based inks, which are miscible. Additionally and in order to increase wear resistance, hardening agents can be added to the ink designed specifically to improve mechanical properties of the ink under sliding contact.

An optimized combination of carbon ink, thinners to lower viscosity, conductive additives, such as silver to lower the electrical resistance and hardeners to improve the mechanical wear are possible with the above described examples to achieve all of the required attributes.

Since the first element 100 is only subject to a rotational or helical movement relative to the second element 200 during one of the first movement and the second movement, e.g. only during setting of a dose the angular position of the first element relative to the second element at the end of consecutive dose dispensing procedures varies every time when the dose dial 180 has been subject to a non-integer revolution relative to the second element 200. As a consequence the position of the electrical contact taps 52, 53, 54, 164, 166, 168 relative to the pattern 104 is subject to regular changes thus inherently reducing the mechanical wear and abrasion as the pattern 106 is subject to a movement relative to the contact taps 52, 53, 54, 164, 166, 168.

Figure 42:
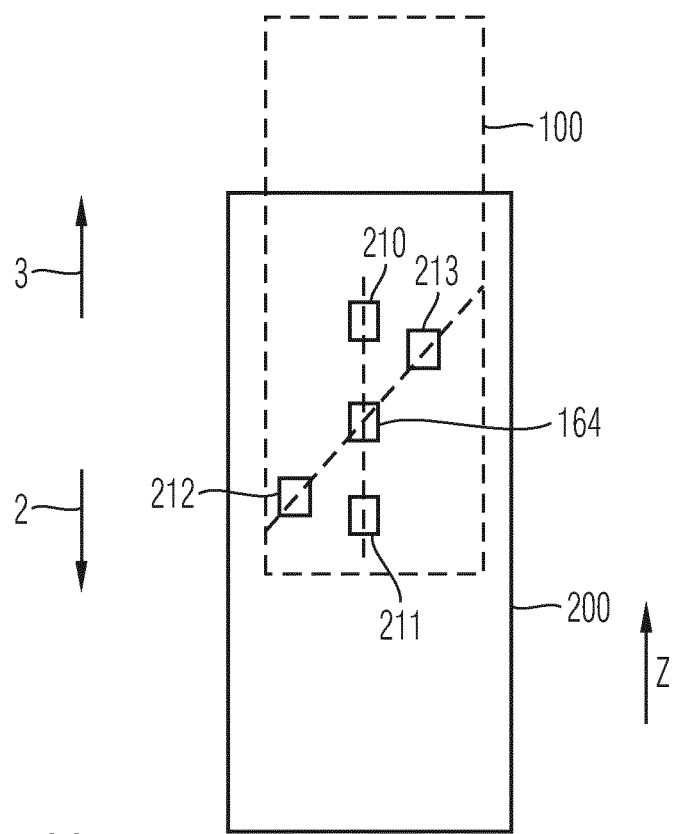

For reducing abrasion and/or wear of the electrically conductive pattern 104 the second element 200 may be provided with at least one cleaning pad 210 located at a distance from the at least one electrical contact taps 52, 53, 54, 164, 166, 168 along at least one of the first movement and the second movement direction. In FIG. 42, such an example is illustrated. The contact tap 164 arranged on the second element 200 is assigned with at least one cleaning pad 210, 211, 212, 213. The cleaning pads 210, 211 are separated in longitudinal direction with regard to the contact tap 164. The cleaning pads 210, 211 are arranged at the same tangential position as the contact tap 164. As the first element 100 is, e.g. subject to a non-rotative longitudinal sliding displacement relative to the second element 200 in distal direction the cleaning pad 211 serves to clean the pattern 104 before it gets in electrical contact with the contact tap 164. As the first element 100 is subject to a sliding and non-rotational movement in the proximal direction the cleaning pad 210 located proximally from the electrical contact tap 164 provides a respective cleaning of the electrically conductive pattern 104.

The same is valid for the further cleaning pads 212, 213 that are arranged along a helical track that matches the helical movement of the first element 100 relative to the second element, e.g. during setting of a dose. Here, the contact tap 213 is tangentially and longitudinally offset from the contact tap 164 in proximal direction. The other contact tap 212 is arranged at a longitudinal distal offset and at a given tangential offset in accordance to the lead of the helical movement between the first element 100 and the second element 200.

Figure 43:
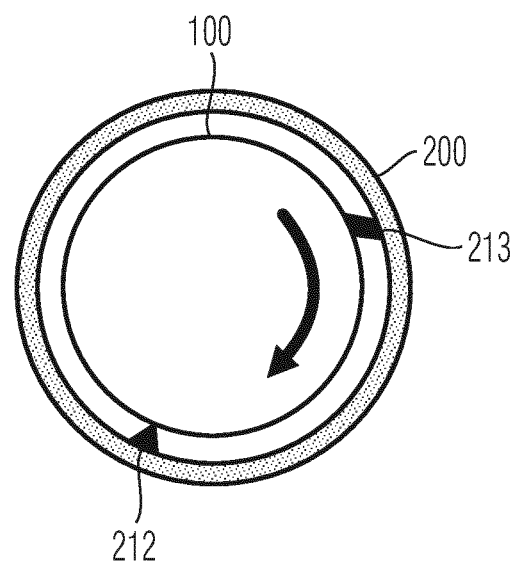
FIG. 43 represents a cross-section through the arrangement of FIG. 42.

As further indicated in a cross-section as illustrated in FIG. 43, the cleaning pads 212, 213 may be at least one of elastically deformable or pivotable with regard to the longitudinal direction as a deformation axis or pivot axis. The cleaning pads 212, 213 may be elastically deformable like a windscreen wiper. As the first element 100 is, e.g. rotated clockwise with regard to the second element 200 the contact surface between the cleaning pad 212, 213 may increase due to an elastic deformation of a radially protruding pointed tip of the cleaning pad 212, 213 or due to a respective swiveling or tilting motion of the respective contact tap 212, 213.

REFERENCE NUMBERS 1 injection device
2 distal direction
3 proximal direction
3 proximal direction
4 dose incrementing direction
5 dose decrementing direction
6 cartridge
7 bung
8 drive mechanism
10 housing
11 trigger
12 dial
13 dosage window
14 cartridge holder
15 injection needle
16 inner needle cap
17 outer needle cap
18 protective cap
20 piston rod
25 barrel
26 seal
28 socket
50 detector arrangement
51 electric sensor
52 contact tap 53 contact tap
54 contact tap
55 switch
56 switch
57 switch
60 reference element
100 first element
102 tubular surface
104 pattern
106 outside surface
110 pattern portion
111 pattern connecting portion
112 pattern portion
114 pattern portion
116 pattern portion
120 pattern section
121 separation
122 pattern section
124 stripe pattern
126 stripe
130 ridge
132 groove
150 detector arrangement
151 electric sensor
152 input terminal
154 input terminal
156 supply voltage
160 reference element
161 body
162 bridging contact
163 arm
164 contact tap
165 arm
166 contact tap
167 arm
168 contact tap
180 dial
181 stepped portion
182 dial sleeve
184 head section
185 receptacle
186 electrical contact
187 sidewall
188 battery
190 printed circuit board
191 processor
192 integrated circuit
193 storage
194 cover
195 communication unit
196 closure
200 second element
201 tubular body
202 retaining cap
210 cleaning pad
211 cleaning pad
212 cleaning pad
213 cleaning pad

The invention claimed is:

1. An injection device for setting and injecting pre-set or user-selectable doses of a medicament, the injection device comprising:
an elongated housing defining a longitudinal direction and configured to accommodate a cartridge containing the medicament;
a detector arrangement operable to detect a relative movement between a first element and a second element,
wherein the first element is subject to a first movement relative to the second element along a first longitudinal direction for setting of a dose, wherein the first element is subject to a second movement relative to the second element along a second longitudinal direction for dispensing of the dose, wherein one of the first movement and the second movement is a helical movement, and wherein the other one of the first movement and the second movement is a sliding movement in the longitudinal direction,
wherein the second element comprises at least one reference element fixed to the second element,
wherein the first element comprises a tubular shaped surface provided with a pattern facing towards the reference element,
wherein the detector arrangement comprises at least one electric sensor arranged on one of the first element and the second element and being operable to detect a positional variation of the pattern relative to the at least one reference element and to generate at least one electric signal in response to the positional variation of the pattern during at least one of the first movement and the second movement of the first element relative to the second element.

2. The injection device according to claim 1, wherein the pattern comprises at least a first pattern portion and a second pattern portion non-overlapping with the first pattern portion.

3. The injection device according to claim 2, wherein the first pattern portion and the second pattern portion distinguish with regard to at least one of the following parameters: electrical conductivity, optical transmissivity, optical reflectivity, magnetic susceptibility, electric susceptibility, and radial position with regard to a central axis of the tubular shaped surface.

4. The injection device according to claim 1, wherein a longitudinal extension of the pattern is equal to or larger than a maximum longitudinal displacement of the first member relative to the second member.

5. The injection device according to claim 1, wherein the pattern comprises a first pattern section and a second pattern section, wherein the first pattern section and the second pattern section are arranged non-overlapping on the tubular shaped surface, and wherein the second pattern section is separated from the first pattern section in the longitudinal direction.

6. The injection device according to claim 5, wherein the first pattern section comprises a stripe pattern comprising a number of parallel oriented longitudinal stripes, wherein the longitudinal stripes extend parallel to the longitudinal direction, or wherein the longitudinal stripes extend at a predefined angle with regard to the longitudinal direction.

7. The injection device according to claim 5, wherein the detector arrangement is operable to detect a longitudinal overlapping of the reference element with at least one of the first pattern section and the second pattern section irrespective of a rotational state of the first element relative to the second element.

8. The injection device according to claim 1, wherein the pattern comprises at least a first pattern portion that is electrically conductive and at least a second pattern portion that is electrically insulating.

9. The injection device according to claim 8, wherein the detector arrangement comprises at least one electrical contact tap arranged on the second element and operable to alternately connect to the first pattern portion and the second pattern portion of the pattern when the first element is subject to one of the first movement and second movement relative to the second element.

10. The injection device according to claim 9, further comprising at least one cleaning pad arranged on or in the second element at a distance from the at least one electrical contact tap along at least one of the first movement and the second movement.

11. The injection device according to claim 8, wherein the pattern comprises at least a third pattern portion that is electrically conductive, and wherein the first pattern portion and the third pattern portion are electrically separated.

12. The injection device according to claim 11, wherein the detector arrangement and the at least one electric sensor are arranged on the first element, wherein the at least one electric sensor is electrically connected to the first pattern portion, and wherein the at least one reference element is arranged on the second element and comprises an electrical bridging contact configured to alternately establish and interrupt an electric contact between the first pattern portion and the third pattern portion when the first element is subject to one of the first movement and the second movement relative to the second element.

13. The injection device according to claim 12, wherein the electrical bridging contact comprises a first electrical contact tap and a second electrical contact tap, wherein the first electrical contact tap and the second electrical contact tap are electrically connected.

14. The injection device according to claim 13, wherein the first electrical contact tap and the second electrical contact tap are spatially separated from each other along a first separation direction parallel to a distance between the first pattern portion and the third pattern portion.

15. The injection device according to claim 14, wherein the electrical bridging contact comprises a third electrical contact tap spatially separated from at least one of the first electrical contact tap and the second electrical contact tap along a second separation direction that is non-parallel to the first separation direction.

16. The injection device according to claim 12, wherein the electrical bridging contact comprises a body made of sheet-metal and comprising at least one flexible arm, and wherein at least one of the first electrical contact tap and the second electrical contact tap is arranged at a free end of the at least one flexible arm.

17. The injection device according to claim 12, wherein a length of a longitudinal movement of the first element relative to the second element during the first movement is identical to a length of a longitudinal movement of the first element relative to the second element during the second movement.

18. The injection device according to claim 17, wherein at least one of the contact taps is at a first rotational position relative to the pattern before the first element and the second element are subject to the first movement.

19. The injection device according to claim 18, wherein when the helical movement of the first element relative to the second element during one of the first movement and the second movement comprises a non-integer multiple rotation of the first element relative to the second element, the at least one of the contact taps is at a second rotational position after a completion of the second movement, and wherein the second rotational position differs from the first rotational position.

20. The injection device according to claim 1, further comprising the cartridge containing the medicament.

\* \* \* \* \*